(12) United States Patent
Ciuperca

(10) Patent No.: US 12,291,491 B2
(45) Date of Patent: May 6, 2025

(54) HYALOCLASTITE FERTILIZER, HYALOCLASTITE PLANT NUTRIENT, HYALOCLASTITE PLANT SOIL IMPROVMENT AND METHOD OF MAKING AND USING SAME

(71) Applicant: Romeo Ilarian Ciuperca, Atlanta, GA (US)

(72) Inventor: Romeo Ilarian Ciuperca, Atlanta, GA (US)

( * ) Notice: Subject to any disclaimer, the term of this patent is extended or adjusted under 35 U.S.C. 154(b) by 0 days.

(21) Appl. No.: 18/416,240

(22) Filed: Jan. 18, 2024

(65) Prior Publication Data

US 2024/0246875 A1 Jul. 25, 2024

Related U.S. Application Data

(60) Provisional application No. 63/480,578, filed on Jan. 19, 2023.

(51) Int. Cl.
*C05D 1/04* (2006.01)

(52) U.S. Cl.
CPC ..................................... *C05D 1/04* (2013.01)

(58) Field of Classification Search
CPC ... C05D 1/04; C05D 3/02; C05D 5/00; C05D 9/00; C05D 9/02
See application file for complete search history.

(56) References Cited

U.S. PATENT DOCUMENTS

| | | |
|---|---|---|
| 7,754,169 B2 | 6/2010 | Constantz |
| 7,749,476 B2 | 7/2010 | Constantz |

(Continued)

FOREIGN PATENT DOCUMENTS

KR 20180106302 A * 10/2018

OTHER PUBLICATIONS

Sun Silicates "Choosing the Right Growing Medium" <https://sunsilicates.co.za/2018/01/16/choosingtherightgrowingmedium/> Jan. 16, 2018 (Year: 2018).*

Gillman, G. P. "The effect of crushed basalt scoria on the cation exchange properties of a highly weathered soil." Soil Science Society of America Journal 44.3 (1980): 465-468. (Year: 1980).*

(Continued)

*Primary Examiner* — Jennifer A Smith
(74) *Attorney, Agent, or Firm* — Robert E. Richards

(57) ABSTRACT

The invention comprises a method of making a mineral plant nutrient. The method comprises screening or reducing in size basaltic hyaloclastite or intermediate basaltic hyaloclastite to a powder form having volume-based mean particle size of less than or equal to 100 μm; and combining the basaltic hyaloclastite or intermediate hyaloclastite powder with soil. The plant nutrients are absorbed by the crop and the carbonatable minerals released from the hyaloclastite react with $CO_2$ from the ground and air. Elements weathered into the separate plant nutrients and carbonatable elements. Plant nutrients such as K, P, S, B, Co, Cu, Fe, Mo, Zn and Ni are used by the crop plants as nutrients. Carbonatable elements such as Ca, Mg, K, Na and Fe react with $CO_2$ from the hyaloclastite, in the ground and the air to create simple or complex carbonated mineral, thereby mineralizing $CO_2$ Optionally, the hyaloclastite can be substituted with lava, scoria, volcanic ash or pumice containing carbonatable elements that when dissolved in soil can react with $CO_2$ and create simple or complex carbonate minerals thereby mineralizing or sequestrating $CO_2$.

20 Claims, 2 Drawing Sheets

(56) References Cited

U.S. PATENT DOCUMENTS

| | | |
|---|---|---|
| 8,470,275 B2 | 6/2013 | Constantz |
| 9,822,037 B1 | 11/2017 | Ciuperca |
| 10,246,379 B2 | 4/2019 | Niven |
| 10,350,787 B2 | 7/2019 | Forgeron |
| 10,570,064 B2 | 2/2020 | Monkman |
| 10,654,191 B2 | 5/2020 | Niven |
| 11,884,602 B1 | 1/2024 | Ciuperca |
| 11,986,769 B1 | 5/2024 | Ciuperca |
| 2019/0100469 A1* | 4/2019 | De La Torre ........... C05F 11/08 |
| 2020/0165170 A1 | 5/2020 | Niven |
| 2020/0223760 A1 | 7/2020 | Monkman |
| 2021/0002171 A1* | 1/2021 | Ciuperca ................... C04B 7/51 |
| 2022/0065527 A1 | 3/2022 | Forgeron et al. |
| 2022/0194852 A1 | 6/2022 | Thomas |
| 2022/0339576 A1 | 10/2022 | Bergur |
| 2022/0340488 A1 | 10/2022 | Bullerjahn |
| 2022/0364441 A1 | 11/2022 | Nagra |

OTHER PUBLICATIONS

Al-Solimani, Samir G., and Saleh H. Byari. "Effect of pozzolan and nitrogen fertilizer in reducing irrigation water and soil moisture stress in three eggplant cultivars (*Solanum melongina*)." Met., Env. & Arid Land Agric. Sci 23.2 (2012): 3-13. (Year: 2012).*
Google Patent English-Lanugage Machine Translation of KR2018106302A. Jan. 22, 2025 (Year: 2025).*
English-Lanugage Machine Translation of KR2018106302A,. Jan. 22, 2025 (Year: 2025).*
U.S. Appl. No. 18/423,001, filed Jan. 25, 2024.
U.S. Appl. No. 18/588,915, filed Feb. 27, 2024.
U.S. Appl. No. 18/612,108, filed Mar. 21, 2024.
U.S. Appl. No. 18/643,867, filed Apr. 23, 2024.
U.S. Appl. No. 18/643,926, filed Apr. 23, 2024.
U.S. Appl. No. 18/495,435, filed Oct. 26, 2023.
U.S. Appl. No. 18/421,638, filed Jan. 24, 2024.
U.S. Appl. No. 18/737,977, filed Jun. 8, 2024.
U.S. Appl. No. 18/670,405, filed May 21, 2024.

* cited by examiner

HYALOCLASTITE FERTILIZER, HYALOCLASTITE PLANT NUTRIENT, HYALOCLASTITE PLANT SOIL IMPROVMENT AND METHOD OF MAKING AND USING SAME

CROSS-REFERENCE TO RELATED APPLICATIONS

This application claims the benefit of application Ser. No. 63/480,578 filed Jan. 19, 2023.

FIELD OF THE INVENTION

The present invention generally relates to the use of hyaloclastite with a basaltic, intermediate or andesitic chemistry as a plant nutrient. The present invention generally relates to the process of manufacturing a natural plant nutrient, as well as the blending or combining a mineral soil into a mix that includes a natural plant nutrient from hyaloclastite or a volcanic mineral with a basaltic, intermediate or andesitic chemistry. More particularly, the present invention relates to an improved soil for plant growth containing hyaloclastite or a volcanic mineral with a basaltic, intermediate or andesitic chemistry. The present invention also relates to a method of carbon sequestration or mineralization by combining $CO_2$ into hyaloclastite or a volcanic mineral-based material to create a natural fertilizer and combining it with soil for plant growth. The present invention also relates to a method of sequestering or mineralizing carbon dioxide generated by plant root systems or carbon dioxide present in soil by hyaloclastite or a volcanic mineral with a basaltic, intermediate or andesitic chemistry mixed into the soil. The present invention also relates to the manufacturing of a plant nutrient fertilizer from hyaloclastite or a volcanic mineral with a basaltic, intermediate or andesitic chemistry and adding the plant nutrient to the plant growing soil. The present invention also relates to a plant growing soil composition comprising of plant nutrient fertilizer made from hyaloclastite or a volcanic mineral with a basaltic, intermediate or andesitic chemistry, a soil and one or more conventional fertilizers made from plant nutrients such as nitrogen, potassium, phosphorus and the like typically used in plant growing soil improvements.

BACKGROUND OF THE INVENTION

Soil has been defined in various ways, but the Natural Resources Conservation Service (formally the Soil Conservation Service) offered the following definition in the book Keys to Soil Taxonomy, "Soil is the collection of natural bodies on the earth's surface, in places modified or even made by man of earthy materials, containing living matter and supporting or capable of supporting plants out-of-doors".

Soil, therefore, is a loose mass of broken and chemically weathered rock mixed with organic matter. Humus is partially decomposed organic matter and is most abundant in topsoil. In wet places in humid regions, plant residue may accumulate several feet thick to form a peat soil; but in dry regions, organic matter may be low to non-existent throughout the landscape. In porous soil, seeds germinate and roots grow as they obtain water and nutrients. It is in this way that we rely on the soil for all the crops we need for food and fiber.

Soil is also an air-storage as well as carbon dioxide storage facility. Plant roots and billions of other organisms living in the soil need oxygen. The pore system in soil provides access to air, which is pushed into and drawn out of the soil by changes in barometric pressure, by turbulent wind, by the flushing action of rainwater, and simply by diffusion. Soil air contains carbon dioxide gas in considerable amounts, which some bacteria can use as it a source of carbon for their protoplasm.

Chemical reactions, primarily involving dissolved oxygen and acids, take place on the ever-increasing surface area of the particles of disintegrating rock. Minerals in the rocks become altered into other forms, and to some extent, the rocks are dissolved and washed away. These naturally occurring physical and chemical forces cause rock weathering. Weathering is the process by which altered rock material may accumulate over the parent rock, or it may be washed or blown to other sites. Soil formation begins at once on the loose rock material (regolith), no matter whether it formed in place or was transported.

Soil has two major solid components: minerals and organic matter. These solid components occupy about half the volume of the soil. Pore space filled with air and water accounts for the other half. Mineral matter makes up the bulk of the solids in most soils.

Soil formation processes alter both rock materials and added organic materials into layers called soil horizons. The number and properties of these horizons vary widely, but a rather typical example is discussed in this section. Dark humic materials commonly accumulate in the topsoil (the A horizon), followed by a leached zone (E horizon from the word eluvial meaning washed out). The sub-soil (B horizon) commonly has an accumulation of clay. Leaching of plant nutrients such as potassium and calcium takes place as water moves through the soil, but some are retained by the finely divided humic and clay materials. Plants take up these nutrients and transport them into their aboveground parts. The nutrients are returned to the soil as the seasons progress; thus, plants contribute to nutrient recycling. This biotic cycling helps to keep the soil from becoming infertile by frequent leaching of organic elements. Weathering continues in the true soil (A through B horizons) as well as below it. As soil ages, it is likely to have a higher clay content because clay results from the physical and chemical breakdown of larger particles. Over time as the soil ages, plant nutrients are depleted and soil may become unsuitable for plant growth. In such cases soil is improved by adding various minerals and elements needed for plant growth, such as fertilizers.

Soils have been formed over the millennia and longer. It is a very slow process. There are a number of factors at work in soil formation. Parent material is the bedrock that has been either slowly broken up at a site or transported there by water or other natural agents. Soil has developed from this parent material. Parent material of mineral soils can be grouped into (1) crystalline rocks, (2) sedimentary rocks, and (3) recent cover deposits.

Crystalline rocks include ancient granites, gabbros, basalts, and associated metamorphic rocks that make up the foundation of the continents. Crystalline rocks underlie the regolith (unconsolidated rock material) on about one-quarter of the earth's land area. Soils that have formed from granite contain a full range of particle sizes, from gravel and sand to the finest clay. Quartz mineral grains (somewhat like bits of glass) in granite are very resistant to weathering and so become the gritty sand in the soil. The other less-resistant minerals in this rock, such as feldspar (a word meaning field crystal because it is so abundant), and dark minerals rich in iron and magnesium (ferromagnesian minerals), including black mica are altered by weathering to fine clay particles.

Black and dark gray crystalline rocks include gabbro (coarse grained) and basalt (fine grained). Because these rocks contain no quartz, the soils formed from gabbro and basalt are not sandy but are clayey and sticky and commonly quite red and rather fertile.

Sedimentary rocks or bedrock underlie the regolith on about three quarters of the land area of the earth. These rocks were deposited as soft layers of sediment on the bottoms and shores of ancient seas. Sand was deposited near the shores, gray mud farther out, and limy white mud very far from shore in the clear water. These layers gradually hardened to rock in most places, becoming sandstone, shale, and limestone, respectively. The sea bottom, thereby slowly uplifted, became dry land. Weathering and erosion of the sedimentary rocks began, and soils formed from them in the process. Soils on sandstone are sandy; those on shale are clayey. Soils on limestone consist largely of insoluble shale materials that were included as gray mud in the otherwise-soluble rock mass. Therefore, soils on limestone commonly are clayey.

Recent cover deposits are blankets of geologically young sediments that overlie the types of bedrock just discussed. These include (1) cover sand, (2) loess, (3) volcanic ash, (4) glacial drift, (5) alluvium, (6) and colluvium. Cover sands are most common in arid and sub-humid areas. Most were initially deposited by water when massive expanses of sandstone were eroded over a long period. Wind action may shift these cover sands into dune formations, and they can then be referred to as eolian deposits. Loess is a wind-transported deposit that consists mainly of silt that was derived from the floodplains of rivers draining the meltwater from glaciers. These silts have a rich supply of plant nutrient-bearing minerals, and their size is such that they hold much water for crops. Extensive areas of fertile agricultural soils can be found in loess deposits in such places as China, the Mississippi-Missouri valley, and the Danube valley in Europe. Volcanic ash is widespread in Hawaii, Oregon, and Washington in the United States and in Central America, Japan, Indonesia, and many other mountainous areas. The mineralogy of volcanic ash is variable, but most of it develops into high-quality soil for crop production. Glacial deposits, often with a covering of loess, are parent materials of soils in much of the corn belt in North America and the wheat belt of Eurasia. They were left by glaciers (and their meltwaters) that advanced and retreated repeatedly between 1 million and 10,000 years ago. Glaciers carried a lot of rock debris collected by a grinding action on the terrain over which they passed and thus were made of "dirty" ice. An unsorted mixture (till) of stones, sand, silt, and clay was deposited in broad blankets and ridges called moraines. Glacial till is sometimes stony enough to inhibit cultivation, but its fresh supply of minerals provides an abundance of many plant nutrients. Alluvial soils are formed from sediments that were deposited by rivers and streams in valleys throughout the world. Colluvium is a gravity-transported deposit at the base of foothills or mountains, which slid from above to its present location. These deposits are extremely variable in composition but are not geographically extensive.

As soon as a mineral surface becomes exposed, chemical weathering is almost sure to follow. The chemical reactions involving water and minerals are much more destructive to rocks than the physical forces. Water is the medium for the acids, produced by living organisms, which cause minerals to disintegrate and be altered into secondary minerals such as clay. When hydrogen ions of acidic solutions replace base-forming metallic ions in minerals, the process is called hydrolysis. When ions are released from minerals, many of them recombine as salts in the soil solution or, if oxygen is present, a few of them such as iron and manganese oxidize and form oxides. Some of these salts and oxides have a strong tendency to combine with water molecules and thereby expand. This disruptive process is called hydration. Water comes as close as anything to being a universal solvent, thus many minerals in rock simply dissolve, but usually at a very slow rate. Temperature, as a component of climate, has a marked influence on the rate of weathering. Perhaps the most obvious effect is that which occurs in the temperate zone, where essentially no chemical weathering takes place while the ground is frozen during the winter. There also is a well-established rule in chemistry that for every 10-degree rise in temperature on the Celsius scale, the rate of chemical reactions increases by a factor of two to three. For example, the soils of the warmer southern part of the United States are more highly weathered than those in the cooler northern states.

In arid regions, the tan-colored soil is only a little darker on the surface than it is deeper down because meager rainfall provides for only sparse vegetation. Even here, however, there are differences. Salts may whiten the soil surface in lower areas if water containing large amounts of salts evaporates off the surface. On very old geologic surfaces, carbonates may accumulate in the subsoil to form rocklike layers.

In the Mid-West US region, where rain is more common during the growing season, the native prairie grasses with their abundant fibrous roots have made the topsoil thick, dark, and rich in plant nutrients. These soils do not have a leached E horizon. They are, in the main, the most fertile soils in the United States. When fields are plowed, they appear almost black from the abundant humus, and if a road is cut through them, they show that the humus commonly extends 2 or more feet (61 cm) below the surface. These soils are the most fertile also due to the mineral make up originated from the glaciers action of grinding parent rock rich in minerals into a fine silt rich in nutrients that also weathered into a suitable clay composition.

The soil properties that we can see or feel are physical. Chemical properties cannot be seen or felt but can be detected with sophisticated scientific instruments. Chemical properties can be altered to our needs with soil amendments, but physical properties are much more permanent and difficult to change. From a physical standpoint, soil is a three-phase system: solid, liquid, and gaseous. For plants growing on the land, each phase is equally essential for their existence. The solid phase is made up primarily of minerals along with a small amount of humus in most soils. This phase provides a source of nutrients and anchorage for plants and makes up about 50% of the soil volume. The liquid and gaseous phases occupy the other half, and the proportion of each varies as the soil gains or loses moisture. Plants must be able to derive water from the soil and they depend upon the soil pores for the oxygen in their roots. A mixture of the proper amounts of sand, silt, and clay, also known as soil separates, is called a loam. A simple loam without excessive amounts of any ingredient has about 20% clay, 40% silt, and 40% sand. Compared to silt and sand, clay is so sticky that not much is required to give the soil a special texture. Soil texture is the degree of fineness or coarseness of the soil, which is an expression of the relative amounts of sand, silt, and clay.

A textural triangle can be used to show the domains of the various soil textures. The word loam applies to the central area in the lower part of the triangle. We can see that equal amounts of sand, silt, and clay would be a clay loam. A soil with 50% sand, 20% silt, and 30% clay is a sandy clay loam. Additions of humus to a soil (not shown in the triangle) modify soil behavior; sandy soils seem finer textured and clay soils seem coarser textured than they really are (see FIG. 2).

Coarse earth is made up of gravel and stones that have a diameter greater than 1/12 inch (2 μmm). Sand ranges in diameter from 2 mm to 0.05 mm and is divided into five classes (see Table 1 below): the smallest sand grains are only 1/40 the size of the largest, and a wide range in their grittiness can be expected. Sand forms the framework of soil and gives it stability when in a mixture with finer particles. Pure sand, however, does not cling together, so it is easily eroded by water and wind. The quartz in sand contributes no plant nutrients to the soil; the other minerals, such as feldspars, release their nutrients very slowly. Nevertheless, soils that have a lot of feldspar and other weatherable minerals, such as basalt type minerals, in their sand fraction develop a comparatively higher state of fertility over the thousands of years of soil formation. Silt is similar to sand except that it is smaller, having a diameter of 0.050 to 0.002 mm (50 micron to 2 micron). It is usually spherical and mineralogically similar to sand. Silt is too fine to be gritty to the touch but imparts a smooth feel without stickiness. It is fine enough to be suspended in flowing water, but it drops out when the flow is reduced. If silt is disturbed by drifting sand, it can be picked up and carried great distances by strong winds; thus, silt constitutes the main part of loess. Silt particles hold much water in the soils and most of this water is available to be used by plants. Over time, some silt particles break down and release ions to the soil solution, so they also serve as a storehouse for plant nutrients. Clay is a soil separate is for the most part much different from sand and silt, which are just progressively finer and finer pieces of the original crystals in the parent rocks. Clay, on the other hand, is made up of secondary minerals that were formed by the drastic alteration of the original forms or by the recrystallization of the products of their weathering.

TABLE 1

Size limits and description of soil fractions

| Soil fraction | Diameter | Description |
| --- | --- | --- |
| Gravel | Larger than 2 mm | Coarse |
| Sand | 0.05-2 mm | Gritty |
| Silt | 0.002-0.05 mm | Floury |
| Clay | smaller than 0.002 mm | sticky when wet |

M. L. Jackson identified minerals in the clay fraction of soils formed under a wide range of weathering conditions and created a list of minerals called weathering index. Minerals at the top of the list are common in soils with some combination of young age, little or no leaching and cool temperatures. Minerals at the bottom of the list are common in soils on old land forms, in area with high temperatures and rainfall. Clay minerals in index class 1 are abundant only in soils of arid regions. Calcite (index number 2) is the main mineral in limestone and present in many soil parent materials. The minerals in index 3, 4, 5, and 6 are primarily minerals that are common in sand and silt particle size classes but not in clay. Quartz (index class 6) is very resistant to weathering and is thus common in the sand and silt fractions of soils. Clay minerals in weathering index class 7 through 10 are common in many soils of the temperate climates. Clay minerals in classes 10, 11 and 12 are common on old landscapes in tropical climates.

TABLE 2

Jackson's Weathering Index for clay-size mineral particles. Index 1 mineral are the most weatherable; index 13 mineral are the most resistant to weathering.

| Index number | Minerals |
| --- | --- |
| 1 | Gypsum and other soluble salts |
| 2 | Calcite |
| 3 | Olivine, pyroxenes, and amphiboles |
| 4 | Biotite |
| 5 | Orthocalse and plagioclase feldspars |
| 6 | Quartz |
| 7 | Vermiculite and interlayer 2:1 minerals |
| 8 | Al-interlayer and similar clay minerals |
| 9 | Smectite |
| 10 | Kaolinite |
| 11 | Gibbsite |
| 12 | Hematite |
| 13 | Zircon, garnet, anatase, and other very resistant minerals |

We speak of mineral soils and organic soils. The difference lies in the amount of organic matter present. Arbitrarily, we say that about 25% organic matter by weight is the dividing point. Soils with more organic matter are called organic soils (peats, mucks). Soils with less are called mineral soils because they are composed mostly of bits of minerals and rocks. The volume of organic matter is about double its weight. Thus, a soil with 5% organic matter by weight has about 10% organic matter by volume.

The common plant nutrient elements calcium, magnesium, and potassium are derived from rock particles. They are taken up by plants, built into living tissue, and returned to the soil when the plants die and then decompose. In the case of nitrogen, rock particles are not the source, but rather the atmosphere, which consists of 78% of this element in gaseous form. The nitrogen cycle is from the air to special bacteria in the soil and some plant roots; to plants; and, through decomposition of the plants, back to the soil, and under certain conditions, back to the atmosphere. Legumes such as clover, alfalfa, peas, beans, and locust and alder trees are primary hosts for symbiotic nitrogen-fixing bacteria (*Rhizobia*). Most grasses, including grain crops, are not natural hosts for nitrogen-fixing bacteria. Small amounts of nitrogen also are fixed outside root nodules. Nitrogen in the form of protein cannot be taken up by higher plants but can become a source of nutrition for a variety of soil microorganisms that consume the protein and release most of the nitrogen as ammonia through their metabolic processes. A substantial amount of the ammonium in the soil is used by two specialized kinds of bacteria, which derive energy by oxidizing ammonium to nitrate ions ($NO_3-$) in a two-step process called nitrification. Most plants absorb nitrogen from the soil in this nitrate form.

The colloidal system of the soil constitutes solid particles that are so finely divided that their diameter is <0.0001 mm (1 Nano). Thus, the colloidal system is made up of the finest clay particles and highly decomposed humus. These colloids are the most chemically active fraction of the soil and are intimately associated with many reactions involved in plant nutrition.

Mineral particles such as common feldspar grains from granite are made up mostly of three elements: silicon, oxygen, and aluminum. Therefore, they are called aluminosilicates. Small feldspar particles slowly change to clay minerals by weathering. Most silicate clay particles are sandwich-like, with two silica layers (silicon plus oxygen) between which is an alumina layer (aluminum plus oxygen).

These clays are called 2:1 clays because of the sandwich-like arrangement. Smectite and hydrous mica are clays of this type. Another clay type is a 1:1 clay, which is used in pottery. There is a single silica layer fastened to a single alumina layer. Kaolinite is a common 1:1 clay.

Because the clay fraction is the seat of most chemical and physical reactions in soils, it is important to know the mineralogy of the clays and why they act as they do.

Montmorillonite is a common member of the smectite group. It is a 2:1 type clay with a high capacity to hold plant nutrients and to absorb water that causes to swell and shrink on wetting and drying. Smectite clays tend to be associated with the climatic regions that have produced grasslands in the United States. When found in the more humid regions, they are generally in soil formed from shale or in the residue from basic rocks.

Oxide clays and hydrated oxide clay minerals also are present in soils. Normally, these are oxides of iron and aluminum and are found most abundantly in soils formed from parent materials rich in iron and aluminum in tropical and subtropical regions where weathering has removed much of the silica from the clay fraction. Oxide clays have little or no crystallinity and very low capacity to hold plant nutrients.

Basic (alkaline) soils have a concentration of hydroxyl ions (OH—) in excess of hydrogen ions. Soils that create a problem by being too alkaline are found scattered in dry areas, but even in arid and semiarid regions, most soils have a favorable pH unless abundant sodium was inherited from the parent material or applied in irrigation water. The pH scale extends from 1 to 14 with pH 7 being neutral. This means that at pH 7 the concentration of hydrogen and hydroxyl ions is equal. As hydrogen ions increase in concentration and hydroxyl ions decrease, the pH drops below 7 and vice versa. Most productive agricultural soils are in the pH range of 5.5 to 8.3.

In arid and semiarid regions of the world, most soils are basic (alkaline) or nearly neutral for two reasons: the ions derived from weathering of minerals are predominantly base-forming ions, and there is not enough precipitation to leach them from the soil. In humid regions of the world, leaching by precipitation causes the bases to be translocated deeper into the soil, and ultimately they return to the sea. We can see the effect of this process over the long span of geologic time in deposits of limestone and other basic sedimentary rocks laid down on the sea bottom.

There are generally three types of clay in soils in the United States: kaolinite, illite, and smectite (montmorillonite). Each clay type has a different capacity to hold nutrients (called the exchange capacity). The exchange capacity is relatively low for kaolinite (2 to 10 mEq/100 g), moderate for illite (20 to 30 mEq/100 g), and high for smectite (80 to 100 mEq/100 g). It follows that a soil with 20% clay as smectite would have a much greater capacity to hold nutrients than a soil with 20% clay as kaolinite. The clay content and the type of clay are both important in soil fertility.

Organic matter is another important soil characteristic that, if high enough in content, can favorably impact the availability of nutrients. Humus (the colloidal fraction) is similar to clay particles in that it has an exchange capacity ranging from 50 to 200 mEq/100 g (depending on the pH of the soil) and attracts and holds nutrients. It provides an exchange complex: organic matter decomposes and breaks down to provide the essential plant nutrients it contains and organic acids are formed, which increases the availability of most nutrients.

At least 16 elements, called plant nutrients, are essential for plant growth. The first group, called basic nutrients, includes three elements carbon, hydrogen, and oxygen, which are the basic building blocks of all plant compounds. The initial product of photosynthesis is the simple sugar $C_6H_{12}O_6$. The carbon comes from carbon dioxide, and the hydrogen and oxygen come from water. The oxygen in the carbon dioxide is given off by plants and goes back into the atmosphere. This process assures us of a continuing source of oxygen.

TABLE 3

Elements required for plant growth

| Basic nutrients | Primary nutrients | Secondary nutrients | Micronutrients |
| --- | --- | --- | --- |
| Carbon (C) | Nitrogen (N) | Calcium (Ca) | Boron (B) |
| Hydrogen (H) | Phosphorus (P) | Magnesium (Mg) | Chlorine (Cl) |
| Oxygen (O) | Potassium (K) | Sulfur (S) | Cobalt (Co) |
| | | | Copper (Cu) |
| | | | Iron (Fe) |
| | | | Manganese (Mn) |
| | | | Molybdenum (Mo) |
| | | | Zinc (Zn) |
| | | | Nickel (Ni) |

The second group of essential elements, called primary nutrients, consists of nitrogen, phosphorus and potassium. They are classified as primary nutrients because they are used in relatively large quantities by plants. The next group of elements are called secondary nutrients and consist of calcium, magnesium and sulfur. These are called secondary nutrients because they are used in smaller quantities by plants than the primary nutrients. Another group of nine elements is called micronutrients because they are normally used in yet smaller quantities. This group includes boron, chlorine, cobalt, copper, iron, manganese, molybdenum, zinc and nickel. Some scientists contend that some other elements also may be essential for plant growth. Included in this group are silicon and sodium. Another group, often called beneficial elements, can be used by plants as substitutes for nutrients that are essential. They include vanadium, iodine, fluorine, and strontium.

Approximately 90% of the dry weight of a plant is made up of carbon, hydrogen, and oxygen; the balance of about 10% consists of the other essential elements. Most of this 10% consists of the elements classified as macronutrients, whereas less than approximately one-tenth of this 10% comes from the micronutrient group. Several elements not known to be essential also may be included in the 10%. Carbon, hydrogen, and oxygen are supplied by carbon dioxide and water.

Each plant nutrient plays one or more special roles in plant growth. A nutrient may be the essential part of a plant compound, thus providing it with a structural base. Calcium, for example, is part of calcium pectate, which is a compound that is a part of the plant cell wall. Other nutrients may be essential for making compounds involved in plant growth processes, such as phosphorus as a part of adenosine diphosphate and adenosine triphosphate, which are two compounds involved in the transfer of energy within a plant. The compounds used for storage of plant foods such as protein require nitrogen and sulfur. Another group is involved in the regulation of certain enzymatic processes. Enzymes in plants, with names such as catalase and lactase, act as catalysts or activators. They often contain micronutrients such as iron and copper, which are part of the enzymes listed above. There are 12 soil orders (the top hierarchical level) in soil taxonomy. The names of the orders end with the suffix -sol. The criteria for the different soil orders include properties that reflect major differences in the genesis of soils. The orders are:

Alfisol—soils with aluminium and iron. They have horizons of clay accumulation, and form where there is enough moisture and warmth for at least three months of plant growth. They constitute 10% of soils worldwide.

Andisol—volcanic ash soils. They are young soils. They cover 1% of the world's ice-free surface. Andisols, derived from a Japanese word Ando which means black soil, are formed from the weathering of volcanic material in minerals in the soil characterized by the poor crystal structure. The materials forming the Andisols have a high capacity to hold nutrients and water making the soil more fertile and very productive. Andisols is made up of weathered soil with much volcanic glass and occur in areas with averagely high rainfall and cool temperatures. They are also easily erodible, especially on the slopes of mountains. Andisols constitute about 1% of the globe and 1.7% of the US glacier-free land.

Aridisol—dry soils forming under desert conditions which have fewer than 90 consecutive days of moisture during the growing season and are nonleached. They include nearly 12% of soils on Earth. Soil formation is slow, and accumulated organic matter is scarce. They may have subsurface zones of caliche or duripan. Many aridisols have well-developed Bt horizons showing clay movement from past periods of greater moisture.

Entisol—recently formed soils that lack well-developed horizons. Commonly found on unconsolidated river and beach sediments of sand and clay or volcanic ash, some have an A horizon on top of bedrock. They are 18% of soils worldwide.

Gelisol—permafrost soils with permafrost within two metres of the surface or gelic materials and permafrost within one metre. They constitute 9% of soils worldwide.

Histosol—organic soils, formerly called bog soils, are 1% of soils worldwide.

Inceptisol—young soils. They have subsurface horizon formation but show little eluviation and illuviation. They constitute 15% of soils worldwide.

Mollisol—soft, deep, dark soil formed in grasslands and some hardwood forests with very thick A horizons. They are 7% of soils worldwide.

Oxisol—are heavily weathered, are rich in iron and aluminum oxides (sesquioxides) or kaolin but low in silica. They have only trace nutrients due to heavy tropical rainfall and high temperatures and low CEC of the remaining clays. They are 8% of soils worldwide.

Spodosol—acid soils with organic colloid layer complexed with iron and aluminium leached from a layer above. They are typical soils of coniferous and deciduous forests in cooler climates. They constitute 4% of soils worldwide.

Ultisol—acid soils in the humid tropics and subtropics, which are depleted in calcium, magnesium and potassium (important plant nutrients). They are highly weathered, but not as weathered as Oxisols. They make up 8% of the soil worldwide.

Vertisol—inverted soils. They are clay-rich and tend to swell when wet and shrink upon drying, often forming deep cracks into which surface layers can fall. They are difficult to farm or to construct roads and buildings due to their high expansion rate. They constitute 2% of soils worldwide.

Soil erosion can be natural or man-made. Natural soil erosion is normal and is called geological erosion. Soil erosion is a serious problem on much of the world's cultivated land.

Soil aging, soil erosion and soil depletion is reducing the quantity of silt and clay in soils suitable for adequate plant growth. Depleted soils can therefore provide and hold less nutrients and less water despite the extensive use of conventional fertilizers.

Therefore, it would be desirable to provide a natural mineral fertilizer of particle size of silt fraction, that in addition to providing essential plant nutrients, can also improve water retention, improve cation and colloidal exchanges and be of such particle size and chemical composition that it can be weathered down to smectite clay fraction in an accelerated timeline to further improve soil properties. It would also be desirable to provide a natural mineral fertilizer that when combined with soil and known or conventional fertilizers such as basic and primary nutrients that improves the plant use of such fertilizers. It would also be desirable to provide a natural mineral plant nutrient that can be tailored and optimized with different types of soils, especially combined with one of the Alfisols, Aridisols, Entisols and Inceptisols type soils and one or more basic, primary or secondary nutrient fertilizer.

SUMMARY OF THE INVENTION

The present invention satisfies the foregoing needs by providing an improved natural mineral fertilizer.

In one disclosed embodiment, the present invention comprises a natural mineral nutrient with a mean particle size sufficiently small or a surface area sufficiently large, particle size falling within the fine sand and mostly silt fraction and with porosity such that it can absorb or adsorb water on the particle surface area to react with and release plant nutrients.

In one disclosed embodiment, the present invention comprises a natural mineral plant nutrient with a chemical composition comprising approximately 40 to approximately 63 percent by weight $SiO_2$, approximately 10 to approximately 18 percent by weight $Al_2O_3$, and approximately 4 to approximately 20 percent by weight CaO and wherein the natural mineral plant nutrient has a mean particle size less than or equal to approximately 100 μm combined with soil used for plant growth and one or more basic, primary or secondary plant nutrient.

In a disclosed embodiment, the present invention comprises hyaloclastite or a volcanic mineral with a basaltic, intermediate or andesitic chemistry and having a mean particle size sufficiently small or a surface area sufficiently large to absorb or adsorb sufficient water on the particle surface area to engage in chemical reactions with primary or secondary nutrients needed for cation exchanges.

In another disclosed embodiment, the present invention comprises a method. The method comprises mixing an aqueous solution and a natural mineral plant nutrient with a chemical composition comprising 40 to approximately 63% by weight $SiO_2$, approximately 10 to approximately 18% by weight $Al_2O_3$, approximately 4 to approximately 18% by weight $Fe_2O_3$, approximately 4 to approximately 20% by weight CaO, approximately 3 to approximately 15% by weight MgO, wherein the natural mineral plant nutrient has a volume-based mean particle size of less than or equal to approximately 100 μm and delivering the aqueous solution to a soil.

In another disclosed embodiment, the present invention comprises a method. The method comprises pelletizing a natural mineral plant nutrient with a chemical composition comprising 40 to approximately 63% by weight $SiO_2$, approximately 10 to approximately 18% by weight $Al_2O_3$, approximately 4 to approximately 18% by weight $Fe_2O_3$, approximately 4 to approximately 20% by weight CaO, approximately 3 to approximately 15% by weight MgO, wherein the natural mineral plant nutrient has a volume-based mean particle size of less than or equal to approximately 100 μm, and delivering the pellet to a soil.

In a disclosed embodiment, the present invention comprises hyaloclastite or a volcanic mineral with a basaltic, intermediate or andesitic chemistry and wherein the hyaloclastite or volcanic mineral has a mean particle size less than or equal to approximately 100 μm combined with Alfisols, Aridisols, Entisols and Inceptisols type soils.

In another disclosed embodiment, the present invention comprises a method. The method comprises providing a soil and a natural mineral plant nutrient from hyaloclastite or a volcanic mineral with a basaltic, intermediate or andesitic chemistry; and wherein the natural mineral plant nutrient has a volume-based mean particle size of less than or equal to 100 μm and comprises at least approximately 4 percent by weight uncarbonated CaO.

In another disclosed embodiment, the present invention comprises a method. The method comprises providing a soil and a natural mineral plant nutrient from hyaloclastite or a volcanic mineral with a basaltic, intermediate or andesitic chemistry, wherein the natural mineral plant nutrient comprises approximately 40 to approximately 63% by weight $SiO_2$, approximately 10 to approximately 18% by weight $Al_2O_3$, approximately 4 to approximately 18% by weight $Fe_2O_3$, approximately 4 to approximately 20% by weight CaO, approximately 3 to approximately 15% by weight MgO, and wherein the natural mineral nutrient has a surface area sufficiently large and porous area to retain a sufficient amount of water to engage in chemical reactions with primary or secondary nutrients needed for cation exchanges.

In another disclosed embodiment, the present invention comprises a method. The method comprises delivering a natural volcanic mineral comprising approximately 40 to approximately 63% by weight $SiO_2$, approximately 10 to approximately 18% by weight $Al_2O_3$, approximately 4 to approximately 18% by weight $Fe_2O_3$, approximately 4 to approximately 20% by weight CaO, approximately 3 to approximately 15% by weight MgO to a mill suitable for reducing the particle size of the natural volcanic material; processing the natural volcanic material in the mill so that the processed natural mineral nutrient has a volume-based mean particle size of less than 100 μm and combining the natural volcanic mineral with soil.

In another disclosed embodiment, the present invention comprises a method. The method comprises delivering hyaloclastite or a volcanic mineral to a screen or mill suitable for separating or reducing the particle size of the hyaloclastite or volcanic mineral; processing the hyaloclastite or volcanic mineral in the screen or mill so that the processed hyaloclastite or volcanic mineral has a volume-based mean particle size of less than 100 μm and combining the natural volcanic mineral with soil and one or more primary plant nutrients.

In another disclosed embodiment, the present invention comprises a method. The method comprises mixing an aqueous suspension of a natural mineral plant nutrient with a chemical composition comprising of 40 to approximately 63% by weight $SiO_2$, approximately 10 to approximately 18% by weight $Al_2O_3$, approximately 4 to approximately 18% by weight $Fe_2O_3$, approximately 4 to approximately 20% by weight CaO, approximately 3 to approximately 15% by weight MgO, wherein the natural mineral plant nutrient has a volume-based mean particle size of less than or equal to approximately 100 μm and spraying the aqueous suspension on a plant body.

In another disclosed embodiment, the present invention comprises a method. The method comprises preparing an aqueous suspension of a natural mineral plant nutrient with a chemical composition comprising of 40 to approximately 63% by weight $SiO_2$, approximately 10 to approximately 18% by weight $Al_2O_3$, approximately 4 to approximately 18% by weight $Fe_2O_3$, approximately 4 to approximately 20% by weight CaO, approximately 3 to approximately 15% by weight MgO, wherein the natural mineral plant nutrient has a volume-based mean particle size of less than or equal to approximately 100 μm and applying the aqueous suspension to a soil.

In another disclosed embodiment, the present invention comprises a method. The method comprises pelletizing a natural mineral plant nutrient with a chemical composition comprising of 40 to approximately 63% by weight $SiO_2$, approximately 10 to approximately 18% by weight $Al_2O_3$, approximately 4 to approximately 18% by weight $Fe_2O_3$, approximately 4 to approximately 20% by weight CaO, approximately 3 to approximately 15% by weight MgO, wherein the natural mineral plant nutrient has a volume-based mean particle size of less than or equal to approximately 100 μm, and delivering the pellet to a soil.

Accordingly, it is an object of the present invention to provide an improved natural mineral plant nutrient.

Another object of the present invention is to provide an improved soil for growing a plant using a natural mineral plant nutrient.

Another object of the present invention is to provide an improved man-made silt to combine with soil for growing a plant using a natural mineral plant nutrient.

A further object of the present invention is to sequester or mineralize carbon dioxide from the atmosphere or industrial processes into a mineral plant nutrient.

These and other objects, features and advantages of the present invention will become apparent after a review of the following detailed description of the disclosed embodiments and the appended claims.

DETAILED DESCRIPTION OF THE DISCLOSED EMBODIMENTS

Figure 1:
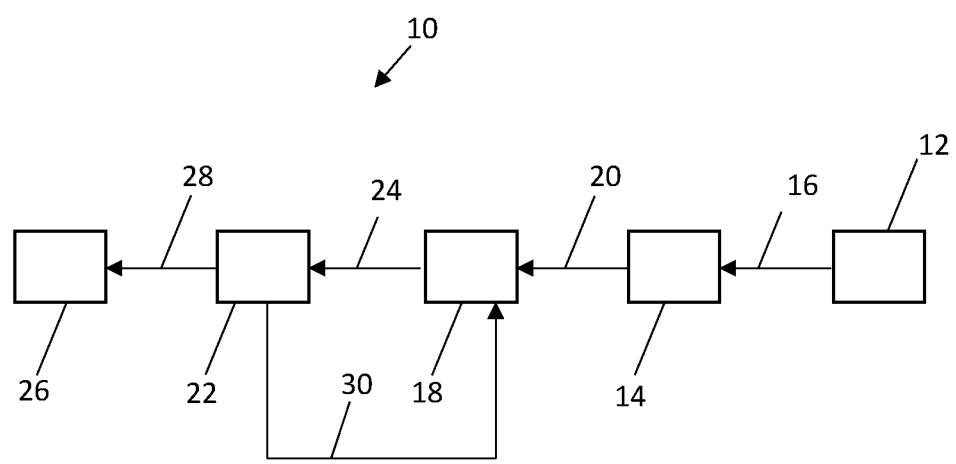
FIG. 1 is flow diagram of a disclosed embodiment of a natural mineral nutrient processing plant in accordance with the present invention.
Figure 2:
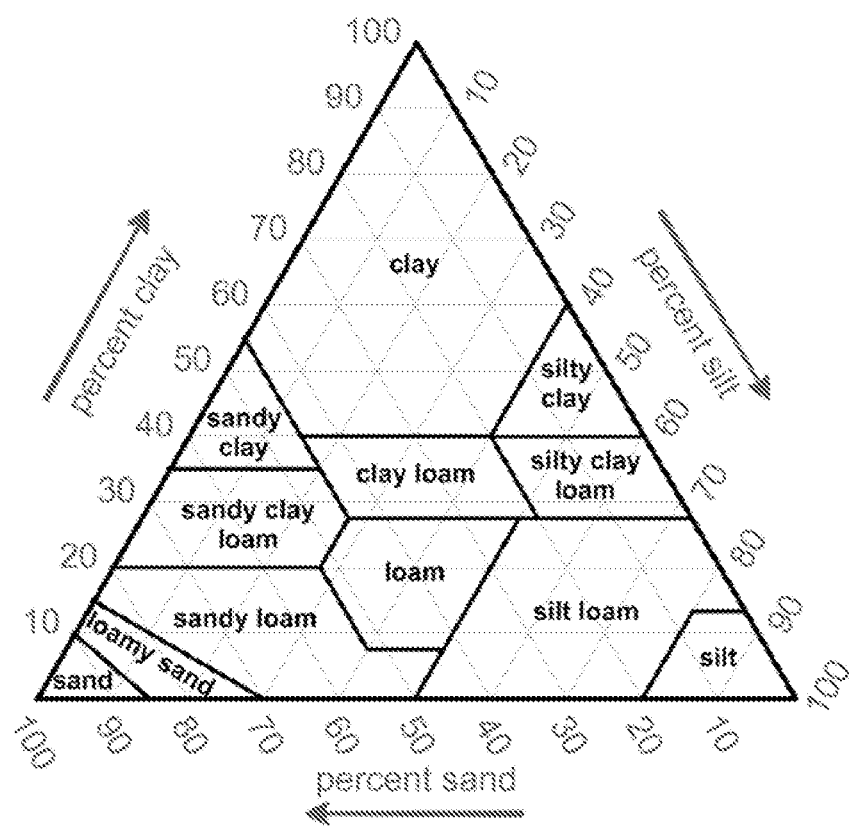
FIG. 2 is a diagram of soil types.

Hyaloclastite is a tuff-like breccia typically rich in black volcanic glass, formed during volcanic eruptions under water, under ice or where subaerial flows reach the sea or other bodies of water. It has the appearance of angular fragments sized from approximately a millimeter to a few centimeters. Larger fragments can be found up to the size of pillow lava as well. Several minerals are found in hyaloclastite masses including, but not limited to, sideromelane, tachylite, palagonite, olivine, pyroxene, magnetite, quartz, hornblende, biotite, hypersthene, feldspathoids, plagioclase, calcite and others. Fragmentation can occur by both an explosive eruption process or by an essentially nonexplosive process associated with the spalling of pillow basalt rinds by thermal shock or chill shattering of molten lava. The water-quenched basalt glass is called sideromelane, a pure variety of glass that is transparent, and lacks the very small iron-oxide crystals found in the more common opaque variety of basalt glass called tachylite. Depending on the type of lava, the rate of cooling and the amount of lava fragmentation, the particle of the volcanic glass (sideromelane) can be mixed with other volcanic rocks or crystalline minerals, such as olivine, pyroxene, magnetite, quartz, plagioclase, calcite and others.

Hyaloclastite is usually found within or adjacent subglacial volcanoes, such as tuyas, which is a type of distinctive, flat-topped, steep-sided volcano formed when lava erupts under or through a thick glacier or ice sheet. Hyaloclastite ridges are also called tindars and subglacial mounds are called tuyas or mobergs. They have been formed by subglacial volcanic eruptions during the last glacial period. A subglacial mound is a type of subglacial volcano. This type of volcano forms when lava erupts beneath a thick glacier or ice sheet. Once the glacier retreated, the subglacial volcano was revealed, with a unique shape as a result of its confinement within the glacial ice. Hyaloclastite breccias are typically products of phreatomagmatic eruptions in particular associated with the eruption of magmas into bodies of water and form by fragmentation of chilled magma. They are often formed from basaltic magmas and are associated with pillow lavas and sheet flows. In addition, any other type of lava, such as intermediate, andesitic, dacitic and rhyolitic, can form hyaloclastite under similar rapid cooling or quenching conditions.

Sometimes a subglacial or subaquatic eruption may produce a release of volcanic ashes that are ejected into the atmosphere which can then land back on the ground. At times a fine volcanic particle size may be called a "volcanic ash" by different professionals in the geological field even though the ash definition may be debatable. It is also possible that a subglacial or subaquatic eruption may have been produced by a magma with high volume of gas entrapped in the lava. The high volume of gas exsolution may create a mineral with very high porosity or vesicular structure and bulk density similar to scoria or pumice.

Natural volcanic minerals, such as lava, hyaloclastite, scoria, or pumice, can be classified based on the amount of silica content as: basaltic (less than 53% by weight $SiO_2$), intermediate (approximately 53-57% by weight $SiO_2$), or silicic such as andesitic (approximately 57-63% by weight $SiO_2$), dacitic (approximately 63-69% by weight $SiO_2$), or rhyolitic (greater than 69% by weight $SiO_2$). However, for the purpose of this invention the basaltic range starts at 40% $SiO_2$ and the andesitic range ends at 65% $SiO_2$.

Basaltic lava, hyaloclastite, scoria or pumice contains generally 40% to 53% by weight silica ($SiO_2$) contained in an amorphous or crystalline form or a combination thereof comprising essentially calcic plagioclase feldspar and pyroxene (usually Augite), with or without olivine. In addition to silica, basaltic lava, hyaloclastite, scoria or pumice generally comprises approximately 10 to approximately 18 percent by weight $Fe_2O_3$, approximately 6 to approximately 18 percent by weight CaO, approximately 5 to approximately 15 percent by weight MgO and other elements in various percentages. Intermediate basaltic lava, hyaloclastite, scoria or pumice generally comprises approximately 53 to approximately 57 percent by weight silica ($SiO_2$) content. In addition to silica, intermediate basaltic lava, hyaloclastite, scoria or pumice generally comprises approximately 5 to approximately 10 percent by weight $Fe_2O_3$, approximately 6 to approximately 10 percent by weight CaO, approximately 3 to approximately 10 percent by weight MgO and other elements in various percentages. Basaltic or intermediate lava, hyaloclastite, scoria or pumice may also contain quartz, hornblende, biotite, hypersthene (an orthopyroxene) and feldspathoids. The average specific density of basaltic or intermediate lava, hyaloclastite, scoria or pumice is approximately 2.5-3.0 gm/cm³.

Andesite is an abundant igneous (volcanic) rock of intermediate composition, with aphanitic to porphyritic texture. In a general sense, it is an intermediate type between basalt and dacite. Andesitic lava, hyaloclastite, scoria or pumice ranges from approximately 57 to approximately 63 percent by weight silicon dioxide ($SiO_2$). For the purpose of this invention, we extend the andesite $SiO_2$ content up to 65%. In addition to silica, andesitic lava, hyaloclastite, scoria or pumice generally comprises approximately 5 to approximately 10 percent by weight $Fe_2O_3$, approximately 5 to approximately 10 percent by weight CaO, approximately 3 to approximately 8 percent by weight MgO and other elements in various percentages. Andesite is the volcanic equivalent of diorite. It consists of the plagioclase feldspar minerals andesine and oligoclase, together with one or more dark, ferromagnesian minerals such as pyroxene, hornblende and biotite. Andesite lava may contain quartz in small amounts. Amygdaloidal andesite occurs when the voids left by gas bubbles in the solidifying magma are later filled in, often with zeolite minerals. Andesite minerals may be fully crystalline or amorphous and a combination of one or more of the crystalline minerals above in various percentage and amorphous glass or mineral.

Dacite is an igneous, volcanic rock with an aphanitic to porphyritic texture and is intermediate in composition between andesite and rhyolite and ranges from approximately 63% to approximately 69% by weight silicon dioxide ($SiO_2$). In addition to silica, dacite generally contains approximately 4 to approximately 8% by weight $Fe_2O_3$, approximately 3 to approximately 8% by weight CaO, approximately 1 to approximately 6% by weight MgO and other elements in various percentages. It consists mostly of plagioclase feldspar with biotite, hornblende, and pyroxene (augite and/or enstatite). It has quartz as rounded, corroded phenocrysts, or as an element of the ground-mass. The plagioclase ranges from oligoclase to andesine and labradorite. Sanidine occurs, although in small proportions, in some dacites, and when abundant gives rise to rocks that form transitions to the rhyolites. The groundmass of these rocks is composed of plagioclase and quartz.

Rhyolite is an igneous (volcanic) rock of felsic (silica-rich) composition, typically greater than 69% by weight $SiO_2$. In addition to silica, rhyolite generally contains 0 to approximately 5% by weight $Fe_2O_3$, approximately 0.5 to approximately 6% by weight CaO, 0 to approximately 2% by weight MgO and other elements in various percentages. It may have a texture from glassy to aphanitic to porphyritic. The mineral assemblage is usually quartz, sanidine and plagioclase. Biotite and hornblende are common accessory minerals.

The different types of volcanic minerals contain varying amounts of uncarbonated elements; i.e., Ca, Mg, K, Na and Fe, that in the presence of $CO_2$ may react to form a carbonate, and, therefore, sequester carbon dioxide when combined with soil. The presence of carbonatable elements can by determined by chemical analysis of oxides. The sum of carbonatable elements is inversely proportional to the $SiO_2$ content. In other words, the higher the silica content the lower the total amount of carbonatable elements which means that a natural mineral nutrient with the lowest silica content will contain the highest amount of uncarbonated Ca and the most amount of one or more uncarbonated elements of Mg, K, Na, Fe, etc. As an example, lava, hyaloclastite, scoria or pumice classified based on the amount of silica content comprises the following elements: basaltic lava, hyaloclastite, scoria or pumice (less than approximately 53% by weight $SiO_2$) contains CaO of approximately 6 to approximately 18% by weight, MgO approximately 5 to approximately 15% by weight, $K_2O$ approximately 1% by weight, $Na_2O$ approximately 3% by weight and $Fe_2O_3$ approximately 10 to approximately 18% by weight; intermediate lava, hyaloclastite, scoria or pumice (approximately 53 to approximately 57% by weight $SiO_2$) comprises CaO of approximately 6 to approximately 10% by weight, MgO approximately 3 to approximately 10% by weight, $K_2O$ approximately 1% by weight, $Na_2O$ approximately 3% by weight and $Fe_2O_3$ approximately 5 to approximately 10% by weight; silicic such as andesitic lava, hyaloclastite, scoria or pumice (approximately 57 to approximately 63% by weight $SiO_2$) comprises CaO of approximately 6 to approximately 18% by weight, MgO approximately 5 to approximately 15% by weight, $K_2O$ approximately 1% by weight, $Na_2O$ approximately 3% by weight and $Fe_2O_3$ approximately 5 to approximately 10% by weight; dacitic (approximately 63 to approximately 69% by weight $SiO_2$) comprises CaO of approximately 3 to approximately 8% by weight, MgO approximately 1 to approximately 6% by weight, $K_2O$ approximately 1% by weight, $Na_2O$ approximately 3% by weight and $Fe_2O_3$ approximately 4 to approximately 8% by weight; while rhyolitic (greater than 69% by weight $SiO_2$) comprises CaO of less than approximately 6% by weight, MgO less than 2% by weight, $K_2O$ approximately 4% by weight, $Na_2O$ approximately 3% by weight and $Fe_2O_3$ approximately 5% by weight. Additionally, the different types of volcanic minerals contain most of the secondary plant nutrients and micro-nutrients when analyzed in accordance with plant fertilizer testing methods, elements such as Ca, Mg, K, P, S, B, Co, Cu, Fe, Mo, Mn, Zn and Ni. These elements are analyzed by digested method using EPA method 3050B and analyzed using EPA method 6010B and 200.7.

The crystalline minerals contained within volcanic lava, hyaloclastite, scoria or pumice with basaltic, intermediate basaltic or andesitic chemistry are on the Jackson weathering index 3-5 on Table 2, (3 olivine, pyroxenes, and amphiboles, 4 biotite, 5 orthoclase and plagioclase feldspars) that when screened or ground to a small particle size in the silt and upper clay fraction, they release the elements contained as plant nutrients Therefore, a natural mineral nutrient from a basaltic, intermediate or andesitic mineral source is far more desirable to be used as a natural mineral plant nutrient in accordance with the present invention than a natural mineral nutrient from a dacitic or rhyolitic source.

In addition, the natural plant nutrient made from a volcanic mineral with a basaltic, intermediate or andesitic chemistry of mean particle size in the silt and upper clay fraction size, of mean particle size of 60 microns or less, and even super fine sand up to 100 microns, when mixed with soil and water as its elements are released as plant nutrients for the plant use, these elements are "leached", weathered or lost from the mineral plant nutrient into the soil. Through this process is the mineral plant nutrient is therefore weathering or altering into a silt or clay of smectite type further enriching the soil that it is in contact with. Smectite clays then are able to retain even more plant nutrients creating some of the most fertile soils as mentioned above. This is a process of soil renewal and is especially important for soils of nutrient depletion and of suitable silt and clay compositions.

As used herein, the term "hyaloclastite" shall mean hyaloclastite from any and all sources; i.e., all hyaloclastites irrespective of the mineral source from which it is derived, unless otherwise designated.

As used herein, the term "volcanic mineral" shall mean lava, hyaloclastite, scoria or pumice from any and all sources; i.e., all irrespective of the mineral source from which it is derived, unless otherwise designated, with an amorphous content of 0-100% and a crystalline content of 0-100% wherein the crystalline matrix is comprised of various types of crystals.

Basaltic or mafic lava, hyaloclastite, scoria or pumice generally has approximately 6% to approximately 18% by weight uncarbonated calcium found with the amorphous matrix or a combination of amorphous and micro crystalline matrix. As the amount of $SiO_2$ increases from the low 40% by weight for basaltic lava, hyaloclastite, scoria or pumice to the andesitic and dacitic silica range, the plant nutrients elements of calcium, magnesium, iron and the like decrease to where in the rhyolitic range there is virtually no suitable plant nutrient elements available to be released into the soil.

Tables 4-5 below show chemical oxides analysis of lava, hyaloclastite, scoria or pumice based natural mineral plant nutrient from various sources and shows CaO levels as well as the $Fe_2O_3$, MgO, correlated with the $SiO_2$ content.

TABLE 4

| Desirable chemical compositions for a natural mineral plant nutrient | | | | | | | | | | |
|---|---|---|---|---|---|---|---|---|---|---|
| Elements | LS36-10 | TDR | SND | AB | BKP | PVT | RDF | THR | VCR | PTR |
| $SiO_2$ | 45.20 | 45.00 | 47.70 | 47.20 | 46.36 | 48.50 | 50.60 | 52.85 | 54.94 | 60.39 |
| $Al_2O_3$ | 14.09 | 17.60 | 15.33 | 12.49 | 11.96 | 15.40 | 15.00 | 14.53 | 14.87 | 13.05 |
| Total $SiO_2$, $Al_2O_3$ | 59.29 | 62.60 | 63.03 | 59.69 | 58.32 | 63.90 | 65.60 | 67.38 | 69.81 | 73.44 |
| CaO | 14.77 | 12.70 | 11.51 | 11.51 | 9.68 | 9.37 | 9.16 | 8.94 | 8.84 | 6.69 |
| MgO | 6.11 | 7.27 | 10.89 | 11.06 | 5.50 | 6.57 | 7.78 | 4.94 | 4.93 | 6.37 |
| FeO | 13.07 | 12.90 | 12.75 | 12.04 | 15.38 | 13.00 | 10.20 | 12.03 | 9.85 | 7.21 |
| Total CaO, MgO, FeO | 33.95 | 32.87 | 35.15 | 34.61 | 30.56 | 28.94 | 27.14 | 25.91 | 23.62 | 20.27 |
| $Na_2O$ | 3.22 | 1.83 | 1.58 | 1.72 | 2.60 | 3.40 | 3.34 | 2.69 | 2.63 | 2.23 |
| $K_2O$ | 1.12 | 0.21 | 0.21 | 0.40 | 0.70 | 1.14 | 1.48 | 0.76 | 0.86 | 2.27 |
| Total Alkali | 4.34 | 2.04 | 1.79 | 2.12 | 3.30 | 4.54 | 4.82 | 3.45 | 3.49 | 4.50 |

All examples above are minerals sampled, processed and analyzed by the inventor from various location around the world. The three-letter designation refers to the mineral source.

The first three samples, LS36-10, TDR and SND, show a basaltic chemistry with the $SiO_2$ of approximately 45-47% and $Al_2O_3$ of 14-17.6% this results in a total silica and alumina content of 59.29-63.03%. The total amount of CaO, MgO and FeO found in these sample total approximately 32.87-35.15%. We call these uncarbonated compounds due to the fact that they do not come from a carbonated mineral source. When ground to a small enough particle size and mixed with water and soil these compounds are available to react with water and soil to release elements that can be used by a plant as nutrients as well as carbonatable elements react with $CO_2$ in the soil to create carbonates. Additionally, when the element contained in the natural mineral plant nutrient of this chemistry used by plants, the mineral plant nutrient is altered from the silt fraction into the clay fraction of smectite type. Smectite type clays are part of the most fertile soil as they retain more nutrients and facilitate most cation exchanges with other plant nutrients to facilitate optimal plant growth.

The next three samples, AB, BKP and PVT, have similar basaltic chemical composition of total silica and alumina of 59.69-63.9% and a total amount of uncarbonated calcium, magnesium and iron oxides of 28.94-34.61%. We call these uncarbonated compounds due to the fact that they do not come from a carbonated mineral source. When ground to a small enough particle size and mixed with water and soil to release elements that can be used by a plant as nutrients as well as carbonatable elements react with $CO_2$ in the soil to create carbonates. Additionally, when the elements contained in the natural mineral plant nutrient of this chemistry used by plants, the mineral plant nutrient is altered from the silt fraction into the clay fraction of smectite type. Smectite type clays are part of the most fertile soil as they retain more nutrients and facilitate the greatest amount of cation exchanges with other plant nutrient to facilitate optimal plant growth. We also note a significant amount an uncarbonated compounds in this chemistry where the ratio between the sum of $SiO_2/Al_2O_3$ and the sum of CaO/MgO/FeO is also approximately 1.72-2.2 to 1. The total sum of the alkalis is also relatively low between 2.12-4.54%. These examples show desirable levels of calcium, magnesium and iron that can be released as plant nutrients to facilitate plant growth. in accordance with the present inventions.

The next two samples, RDF and THR, have similar basaltic chemical composition of total silica and alumina slightly higher of 65.6-67.38% and a total amount of uncarbonated calcium, magnesium and iron oxides of 25.91-27.14%. When ground to a small enough particle size and mixed with water, soil, and primary plant nutrients, the elements contained within are released as plant nutrients to facilitate the plant growth as well as carbonatable elements react with $CO_2$ in the soil to create carbonates. Additionally, when the element contained in the natural mineral plant nutrient of this chemistry used by plants, the mineral plant nutrient is altered from the silt fraction into the clay fraction of smectite type. Smectite type clays are part of the most fertile soil as they retain more nutrients and facilitate most cation exchanges with other plant nutrient to facilitate optimal plant growth. These examples show desirable levels of calcium, magnesium and iron oxides in accordance with the present inventions.

The next example, VCR, has an intermediate chemical composition of total silica and alumina slightly higher of 69.81%. The total amount of uncarbonated calcium, magnesium and iron oxides of 23.62%. When ground to a small enough particle size and mixed with water, soil, and primary plant nutrients, the elements contained within are released as plant nutrients to facilitate the plant growth as well as carbonatable elements react with $CO_2$ in the soil to create carbonates. Additionally, when the element contained in the natural mineral plant nutrient of this chemistry used by plants, the mineral plant nutrient is altered from the silt fraction into the clay fraction of smectite type. Smectite type clays are part of the most fertile soil as they retain more nutrients and facilitate most cation exchanges with other plant nutrient to facilitate optimal plant growth. We also note a significant amount of uncarbonated compounds in this chemistry however the ratio between the sum of $SiO_2/Al_2O_3$ and the sum of CaO/MgO/FeO is higher at approximately 2.9 to 1. The total sum of the alkalis is also relatively low between 3.49%. This example shows a chemical composition with greater capacity for the natural mineral nutrient to release elements to be used as plant nutrients to facilitate plant growth. This examples still shows a sufficiently desirable levels of calcium, magnesium and iron and other elements that can be used as plant nutrients to facilitate plant growth in accordance with the present inventions.

The last example, PTR, has an andesitic chemical composition of total silica and alumina slightly higher of 73.44%. The total amount of uncarbonated calcium, magnesium and iron oxides of 20.27%. When ground to a small enough particle size and mixed with water, soil, and primary plant nutrients, the elements contained within are released as plant nutrients to facilitate the plant growth as well as carbonatable elements react with $CO_2$ in the soil to create carbonates. Additionally, when the element contained in the natural mineral plant nutrient of this chemistry used by plants, the mineral plant nutrient is altered from the silt fraction into the clay fraction of smectite type. Smectite type clays are part of the most fertile soil as they retain more nutrients and facilitate most cation exchanges with other plant nutrient to facilitate optimal plant growth.

The values of the Ca, Mg, Fe, Na and K oxides shown in Table 5 below are examples of less desirable oxide levels for natural mineral plant nutrient in accordance with the present invention.

TABLE 5

Minerals with less desirable natural mineral plant nutrient

| Elements | CR | GP | MLO | GEO | WCL | CDH | MS | WHA | RHA | SF |
|---|---|---|---|---|---|---|---|---|---|---|
| $SiO_2$ | 68.23 | 64.30 | 73.72 | 72.50 | 74.92 | 76.40 | 92.10 | 92.86 | 93.84 | 97.00 |
| $Al_2O_3$ | 14.68 | 15.23 | 12.66 | 11.40 | 13.05 | 12.30 | 2.13 | 1.88 | 1.93 | 0.20 |
| Total $SiO_2$, $Al_2O_3$ | 82.91 | 79.53 | 86.38 | 83.90 | 87.97 | 88.70 | 94.23 | 94.74 | 95.77 | 97.20 |
| CaO | 3.11 | 4.32 | 1.08 | 0.98 | 0.98 | 0.85 | 1.10 | 0.19 | 0.68 | 0.20 |
| MgO | 0.92 | 0.98 | 0.53 | 0.35 | 0.35 | 0.05 | 1.05 | 0.01 | 0.45 | 0.52 |
| FeO | 4.43 | 7.89 | 1.38 | 2.30 | 0.72 | 1.07 | 1.62 | 0.35 | 0.29 | 0.55 |
| Total CaO, MgO, FeO | 8.46 | 13.19 | 2.99 | 3.63 | 2.05 | 1.97 | 3.77 | 0.55 | 1.42 | 1.27 |
| $Na_2O$ | 3.18 | 4.19 | 3.41 | 3.75 | 3.75 | 3.71 | 0.10 | 0.25 | 0.10 | 0.22 |
| $K_2O$ | 2.74 | 1.69 | 3.15 | 4.22 | 4.22 | 5.37 | 1.32 | 0.78 | 1.38 | 0.51 |
| Total Akali | 5.92 | 5.88 | 6.56 | 7.97 | 7.97 | 9.08 | 1.42 | 1.03 | 1.48 | 0.73 |

The first two samples, CR and GP, show a dacitic chemistry with the $SiO_2$ of approximately 64.3-68.23% and $Al_2O_3$ of 14.68-15.3% this results in a total silica and alumina content of 79.53-82.91%. The total amount of CaO, MgO and FeO found in these sample total approximately 8.46-13.19%. When ground to a small enough particle size and mixed water, soil, and primary plant nutrients, the elements contained within are released as plant nutrients to facilitate the plant growth as well as carbonatable elements react with $CO_2$ in the soil to create carbonates. Additionally, when the element contained in the natural mineral plant nutrient of this chemistry used by plants, the mineral plant nutrient is altered from the silt fraction into the clay fraction of smectite type. Smectite type clays are part of the most fertile soil as they retain more nutrients and facilitate most cation exchanges with other plant nutrient to facilitate optimal plant growth. In these two examples it is noted that the total alkali is between 5.88-5.92%. This is a larger amount of alkali than examples in Table 4.

The next four examples, MLO, GEO, WCL and CDH, show a rhyolitic chemistry with the $SiO_2$ of approximately 72.5-76.40% and $Al_2O_3$ of 11.40-13.05% this results in a total silica and alumina content of 83.90-88.70%. The total amount of CaO, MgO and FeO found in these sample are insignificant at a total of approximately 1.97-3.63%. We also note that the ratio between the sum of $SiO_2/Al_2O_3$ and the sum of CaO/MgO/FeO is approximately 23.11-45.3 to 1. In these four examples it is noted that the total alkali is between 6.56-9.08%. This is a larger amount of alkali than the first two example in this table above, and of all examples in Table 4. These are not desirable for the use of mineral plant nutrient in accordance with the present invention.

The next three examples, MS, WHA and RHA, are from the microsilica category. WHA is a wheat husk ash and RHA is a rice husk ash. These show a chemistry with the $SiO_2$ of approximately 92.10-93.84% and a very insignificant amount of $Al_2O_3$ of 1.88-2.13%. This results in a total silica and alumina content of 94.23-95.77%. The total amount of CaO, MgO and FeO found in these sample are also insignificant at a total of 3.77 for the MS and approximately 0.55-1.42%. Regardless of how finely ground the particle size is, when mixed with water, soil, and primary plant nutrients, the elements contained within are not suitable to be released as plant nutrients to facilitate the plant growth. Additionally, when the elements contained in the natural mineral plant nutrient of this chemistry cannot be used by plants, the mineral plant nutrient is not able to be altered from the silt fraction into the clay fraction of smectite type. Therefore, this is not a desirable mineral chemistry to be used as a plant nutrient in accordance with this invention.

Similarly, granite, and quartz minerals are not suitable to be used as a mineral plant nutrient in accordance with the present invention.

Different volcanic minerals, including lava, hyaloclastites, scoria or pumices, have different amounts of amorphous glass and crystalline content. The oxides shown in Tables 4-5 above is a method of determining the chemical composition and may not be a reflection of actual free oxides present within the matrix by themselves. The oxides may be part of complex formula of amorphous or microcrystalline structure or a combination thereof.

If the chemical composition of the mineral plant nutrient is of an amorphous type the elements are easier to release as plant nutrients when combined with water and soil, especially a basic or alkaline soil. When the mineral plant nutrient is of crystalline compositions or a combination of amorphous and crystalline the following crystalline minerals have the following chemical compositions and therefore various elements that can be released and made available as plant nutrients, especially in acidic soils. As these elements are released the mineral plant nutrient then alters into a clay and is farther reduce in size. This process facilitates soil renewal or soil enriching especially for depleted soils or soils of warm or arid climates.

Olivine group minerals, belonging to the isolated tetrahedra silicate subclass, all have similar atomic arrangements. By far, the most important mineral of this group is called olivine. In contrast with some of the other silicates previously discussed, olivine chemistry is quite simple. Its general formula is $(Mg, Fe, Ca, Mn)_2SiO_4$ but often Mn and Ca are omitted because they are normally minor components.

Pyroxenes contain many different elements, but all pyroxenes have the general formula $(Ca, Na, Mg, Fe)(Mg, Fe, Al)(Si, Al)_2O_6$. The most common pyroxenes are close to $Ca(Mg, Fe)Si_2O_6$ or $(Mg, Fe)_2Si_2O_6$ in composition.

Amphiboles and pyroxenes are closely related minerals that commonly coexist. Both are chain silicates, but the atomic arrangement in amphiboles is more complex than in pyroxenes. Like pyroxenes, amphibole chemistry is highly variable and yields many different end member formulas. Just a few are listed in the blue box. Also, like the pyroxenes, amphiboles fall into two main series: the orthoamphibole series and the clinoamphibole series. The amphiboles general formula is (K, Na)$_{0-1}$(Ca, Na, Mg)$_2$(Mg, Fe, Al)$_5$(Si, Al)$_8$O$_{22}$(OH)$_2$ Feldspars are the most abundant minerals in Earth's crust. Their compositions vary but may be described with the general formula (Ca, Na, K)(Si, Al)$_4$O$_8$. Feldspar structures are based on SiO$_4$ and AlO$_4$ tetrahedra linked to form at three-dimensional framework. They form two series that share one end-member composition: the alkali feldspar series (mainly NaAlSi$_3$O$_8$—KAlSi$_3$O$_8$) and the plagioclase (mainly NaAlSi$_3$O$_8$—CaAl$_2$Si$_2$O$_8$) series, alkali feldspars range in composition from albite (NaAlSi$_3$O$_8$) to orthoclase (KAlSi$_3$O$_8$). They also contain minor amounts of anorthite (CaAl$_2$Si$_2$O$_8$). Plagioclase feldspars are mostly solid solutions of albite (NaAlSi$_3$O$_8$) and anorthite (CaAl$_2$Si$_2$O$_8$). They commonly contain lesser amounts of orthoclase (KAlSi$_3$O$_8$), especially at high temperatures K-rich feldspar may be either of three polymorphs: sanidine, orthoclase, or microcline. The three differ in the way SiO$_4$ and AlO$_4$ tetrahedra are distributed in their structures. Sanidine, the high-temperature polymorph, is most disordered; microcline, the low-temperature polymorph, is most ordered. Orthoclase has intermediate and somewhat variable ordering. Na-rich feldspar, too, has different polymorphs; they include monalbite at high temperature and low-albite at low temperature Orthoclase comes from the Greek word orthos (right angle) and klasis (to break), referring to this mineral's perpendicular cleavages. The formula is KAlSi$_3$O$_8$. The luster, hardness, and color of orthoclase may be similar to other feldspars, but (in contrast with plagioclase) orthoclase is frequently tan, pink, or flesh colored (plagioclase is usually white). Orthoclase has cleavage planes that meet at about 90 degrees, like other feldspars, but, orthoclase does not show twin striations like plagioclase does.

Chemical composition as reported herein is measured by the XRF (X-ray fluorescence) method. This is a non-destructive analytical technique used to determine the elemental composition of materials. XRF analyzers determine the chemistry of a sample by measuring the fluorescent (or secondary) X-ray emitted from a sample when it is excited by a primary X-ray source. Each of the elements present in a sample produces a set of characteristic fluorescent X-rays ("a fingerprint") that is unique for that specific element, which is why XRF spectroscopy is an excellent technology for qualitative and quantitative analysis of material composition. The chemical analysis reported herein is the total oxides scan. However, XRF analysis cannot detect the element Boron and for this and more relevant plant nutrient analysis the dissolution methods using EPA method 3050B and analyzed using EPA method 6010B and 200.7 are employed.

Sample preparation for XRF can be achieved using either of two distinct methods: a pressed powder and a fused glass disk. Pressed powder specimens are typically ground in a tungsten carbide ring and puck mill with a binding agent to reduce the particle size and provide a packed powder mount that will remain intact for transport and analysis. The advantages of this preparation method include the simplicity and better detection limits while disadvantages include what is known as the "mineralogical effect", which requires a similar matrix between a bracketed calibration and unknown specimens for the calibrations to be valid.

In case of lava, hyaloclastites, scoria, pumice, etc., containing some degree of crystalline elements, the carbonatable elements are contained in micro-crystals, such as clinopyroxene Ca(Mg,Fe,Al,Ti)(Si,Al)$_2$O$_6$, calcium plagioclase feldspars (Na,Ca)Al(Si,Al)$_3$O$_8$, olivine (Fe,Mg)$_2$SiO$_4$ are examples of crystalline materials that contain uncarbonated elements, such as calcium, magnesium, potassium, sodium and iron, that are available to be released as plant nutrients when combined with water and soil. Alternatively, any of the uncarbonated calcium, magnesium, iron, sodium, potassium may react in any particular fashion and form more complex crystal minerals such as olivine, pyroxenes, plagioclase feldspars, K-feldspars, mordenite, clinoamphibole, ilmenite or other similar crystal minerals. These carbonatable elements, and others, can be found in pumices and hyaloclastites of these chemistries can be in amorphous or microcrystalline form or a combination thereof.

The breakdown, weathering or leaching process of the elements above is accelerated at a higher temperature, such as the in soils of warm climates, to release plant nutrient elements when ground to fine particle size in the silt particle size fraction.

Table 6 below shows examples of hyaloclastites or pumices that contain various amounts of amorphous and crystalline content. Samples 14 and 15 are rhyolitic glass such as perlite and the CaO content is below 1% compared with the basaltic in Samples 1-13 where CaO ranges between 9-16%.

TABLE 6

| | "Amorphous" | Clinopyroxene Ca(Mg, Fe, Al, Ti) (Si, Al)2O6 | Plagioclase Feldspar (Na, Ca)Al(Si, Al)3O8 | Olivine (Fe, Mg)2SiO4 | Calcite | Unidentified |
|---|---|---|---|---|---|---|
| 1 | >70 | — | 12 | 5 | 7 | <5 |
| 2 | >80 | | 10 | <5 | — | <5 |
| 3 | >70 | <3? | 11 | <5 | — | <5 |
| 4 | >80 | — | 13 | <3 | — | <5 |
| 5 | >55 | | 12 | 5 | 20 | <5 |
| 6 | >70 | — | 11 | 5 | <5 | <5 |
| 7 | >75 | — | 10 | 5 | — | <5 |
| 8 | >65 | — | 15 | 5 | <5 | <5 |
| 9 | >70 | <3? | 12 | 5 | | <5 |
| 10 | >30 | 25 | 43 | 5 | | <5 |
| 11 | >55 | | 15 | 5 | 15 | <5 |
| 12 | >40 | 17 | 37 | 4 | 1 | <5 |
| 13 | >70 | — | 15 | 8 | | <5 |
| 14 | >95 | | | | | <5 |
| 15 | >95 | | | | | <5 |

A basaltic hyaloclastite sample was taken from a natural mineral deposit and processed into a mineral plant nutrient in accordance with the present invention. From the same mineral deposit three different particle size plant nutrients were made. First, a fine sand of approximately 100 microns was screened from the natural mineral deposit. Second, a 1-2 mm sand particle size was screened from the natural hyaloclastite mineral deposit. Screening using mesh screens or any other type of equipment is a process well known to persons skilled in the art for separation a granular product into desired particle size ranges. The equipment for preforming such screening is also commercially available and well known to a person of ordinary skill in the art. Third, a 20-micron volume-based mean particle size was processed by using a vertical Raymond Mill. Each one of these samples was analyzed and then the combination of the three in the configurations described below were also analyzed for a total of six different samples.

Mineral plant nutrient samples were prepared and analyzed by a third-party fertilizer and soil analysis laboratory. Total nitrogen analyzed using AOAC 990.3. For all other elements listed below, samples are digested using EPA method 3050B and analyzed using EPA method 6010B and 200.7.

processing of the hyaloclastite into a finer powder shows a greater availability of nutrients.

Fourth, sample F4 is a combination of half F1 and half F2, meaning that the 20 microns volume-based mean particle size ground powder was combined in equal amount with 100 micron screened fine sand. In this combination some elements are in greater quantity available than in the F1 or F2 alone while others in similar quantities. This sample shows that the combination of screened and ground mineral plant nutrient with a volume-based mean particle size of approximately 60 micron provides a greater nutrient plant availability then the screened 100 μmicron size with less ground mineral than the 20 micron mean particle size sample F2.

Fifth, sample F5 is a combination of half F2 and half F3, meaning that the 20 micron volume-based mean particle size ground powder was combined in equal amount with 1-2 mm screened sand. In this combination some elements are in greater quantity available than in the F1 or F3 alone than others in similar quantities. This sample shows that the combination of screened and ground mineral plant nutrient with a volume-based mean particle size of approximately 80

TABLE 7

Plant nutrient samples analysis:

| Elements | Sample | | | | | |
|---|---|---|---|---|---|---|
| | F1 | F2 | F3 | F4 | F5 | F 6 |
| TOTAL NITROGEN, % | 0.039 | 0.025 | 0.030 | 0.030 | 0.030 | 0.200 |
| TOTAL P2O5, % | 0.062 | 0.054 | 0.045 | 0.088 | 0.073 | 0.071 |
| TOTAL K2O, % | 0.360 | 0.300 | 0.180 | 0.350 | 0.270 | 0.280 |
| WATER SOLUBLE SO4—S, % | 0.033 | 0.072 | 0.028 | 0.023 | 0.036 | 0.029 |
| TOTAL CALCIUM, % | 1.980 | 5.850 | 5.900 | 3.750 | 6.300 | 4.990 |
| TOTAL MAGNESIUM, % | 1.460 | 2.080 | 1.470 | 2.020 | 2.010 | 1.880 |
| TOTAL SODIUM, % | 0.200 | 0.600 | 0.340 | 0.630 | 0.660 | 0.570 |
| TOTAL ZINC, ppm | 32 | 41 | 30 | 44 | 39 | 37 |
| TOTAL IRON, ppm | 19412 | 25883 | 21788 | 37467 | 34719 | 32450 |
| TOTAL MANGANESE, ppm | 427 | 513 | 380 | 640 | 584 | 554 |
| TOTAL COPPER, ppm | 9.0 | 16.0 | 6.0 | 7.0 | 4.0 | 3.0 |
| TOTAL BORON, ppm | 9.0 | 22.0 | 2.0 | 2.0 | 0.4 | 0.7 |

First sample, F1 (PVT 100 microns) was screened using a wire screen passing 140 mesh meaning the screen size opening passed a sample particle size less than 104 microns, taken from the natural deposit and analyzed for the nutrients without any other processing. The element values are shown in column F1.

Second sample F2 (PVT PWR) was taken from the same material and was processed using a vertical Raymond mill to a volume-based mean particle size of 20 microns. The elements are shown in column F2. As shown above, some of the nutrients, such as Ca, Mg, Na, Zn, Fe, Mn, Cu and B are available in greater quantities in the finer particle size F2 compared with the coarser particle size F1 in the mineral plant nutrients.

The third sample, F3 (PVT 1-2 mm), was screened using a wire screen passing 10 mesh meaning the screen size opening passed a sample particle size less than 2 mm and retained by screen mesh size 18, meaning the material has the size between 1 mm to 2 mm taken from the natural deposit and analyzed for the nutrients without any other processing. The elements are shown in column F3. Most of the elements measured in sample F3 are in a quantity less than the quantity of elements shown in sample F2. Similarly, the quantity of most of the elements shown in sample F3 are less than the elements in sample F1 although the difference is less between F3 and F1 than F3 and F2. Thus, the μmicron provides a greater nutrient plant availability then the screened 1-2 mm size with less ground mineral than the 20 micron mean particle size F2 sample.

Sixth, sample F6 is a combination of one third F1, one third F2 and one third F3, meaning that the 20 micron volume-based mean particle size ground powder was combined in an equal amount with the 100 micron screened fine sand and an equal amount of 1-2 mm screened sand. In this combination, some elements are in greater quantity available than in the F1 or F3 alone than others in similar quantities. This sample shows that the combination of screened and ground mineral plant nutrient with a volume-based mean particle size of approximately 100 micron provides a greater nutrient plant availability then the screened 1-2 mm size or 100 micron with less ground mineral than the 20 micron mean particle size F2 sample.

Referring now to FIG. 1, there is shown a flow diagram of a disclosed embodiment of a natural mineral nutrient processing plant 10 in accordance with the present invention. A natural volcanic mineral, such as lava, hyaloclastite, scoria or pumice is mined from the ground at a mine site. Unprocessed volcanic mineral may have a particle size of about 100 micron to ½ an inch or in the range a very fine sand to gravel. It may also have a larger size of lava pillows or breccia. The volcanic mineral is transported from the mine site to the natural mineral plant nutrient processing plant 10 where it is deposited in a supply pile 12. The volcanic mineral in the supply pile 12 may have a moisture content of approximately 2 to 20% by weight. The volcanic mineral of particle sizes larger than sand may be reduced in size down to a 1/32 to 1/4" size by using a rock crusher. Optionally the volcanic mineral can be screened using a particle size separator, such as a mesh screen, classifier or the like to remove the fine sand and silt fraction from the coarser size material. As such, under certain conditions a mineral plant nutrient can be achieved by separating the 60-150 micron particles to create a mean particle size of 100 micron or less material without having to grind it therefore saving energy and time. However, in order to reduce the particle size of the unprocessed volcanic mineral to the finer silt size in the micron range by a dry process mill, it must have a moisture content of approximately 5% by weight or lower. Therefore, it may be necessary to dry the unprocessed volcanic mineral. Accordingly, unprocessed volcanic mineral from the supply pile 12 is transported from the pile to a dryer 14 by a conveyor belt 16. The dryer 14 is typically a rotating drum or fluid bed (not shown) with a gas flame that projects into the drum or fluid bed or by an electric heating element. Helical flights or conveyer belts within the drum or fluid bed dryer move the hyaloclastite, or pumice, from the inlet of the drum or fluid bed to the outlet. The temperature inside the dryer is sufficiently high to allow for the desired reduction in moisture based on the moisture content of the materials fed into the dyer. From the dryer 14, the dried lava, hyaloclastite, scoria or pumice is transported to a micronizing mill 18 by either a conveyor belt or a screw conveyor 20. The mill 20 reduces the particle size of the lava, hyaloclastite, scoria or pumice, from the 100 micron—1/2" size it was screened after it was mined or pre-crushed by a rock crusher, to a desired particle size in the micron range. The micronizing mill can be a ball mil, a roller mill, a rod mill or any other type mill that can reduce a mineral down to the desired particle size. If a high aspect ratio particle size is desired to then a vertical roller mill is more desirable type mill to employ for the production of the natural mineral plant nutrient. The micronizing mill may be a dry process mill circuit as described above or it can be a wet process mill circuit. From the mill 18, the reduced size lava, hyaloclastite, scoria or pumice, is lifted by the air flow into a particle size classifier 22 connected by a duct or pipe 24. The classifier separates particles that meet a desired size criteria from those that do not meet the criteria. Those particles that meet the size criteria are passed from the classifier 22 to a storage silo 26 by air flow or a screw conveyor 28. Those particles that are bigger than the size criteria are transported from the classifier 22 back to the input of the micronizing mill 18 by a retuning duct or pipe 30. The storage silo 26 is used to contain the lava, hyaloclastite, scoria or pumice natural mineral plant nutrient of the desires particle size range until it can be transported, such as by rail or truck, to a customer. If a wet process mill circuit is used then the natural mineral plant nutrient will be in liquid form instead of a powder form, however the particle size will be the same. Alternatively, the mineral can be processed using a wet mill process and the classification technology associated with wet processing known in the industry.

In a disclosed embodiment, the present invention comprises a natural mineral plant nutrient from a lava, hyaloclastite, scoria or pumice with a chemical composition preferably comprising approximately 40 to approximately 63 percent by weight $SiO_2$, approximately 10 to approximately 18 percent by weight $Al_2O_3$, 4 to approximately 20 percent by weight CaO, and optionally one or more of approximately 3 to approximately 15% MgO and approximately 4 to approximately 18 percent by weight $Fe_2O_3$, ground into powder form. The particle size of the natural mineral nutrient powder is sufficiently small such that the hyaloclastite or pumice powder has natural mineral nutrient properties. The natural mineral plant nutrient particle size in either dry powder or wet suspension or dispersion, preferably has a volume-based mean particle size of less than or equal to approximately 100 μm, less than or equal to approximately 60 μm, of approximately 40 μm, of more approximately 20 μm, more preferably less than or equal to 16 μm, most preferably less than or equal to 12 μm, especially less than or equal to 10 μm, more especially less than or equal to 8 μm and most especially less than or equal to 4 μm. The smaller the particle size for the natural mineral plant nutrient particle size in either dry powder or wet suspension or dispersion, the greater the surface area to retain water and react with soil to release secondary plant nutrient and micronutrients elements contain in the natural mineral natural mineral nutrient. However, there are economic limits for grinding rock to small particle sizes. Those limits are well known by those skilled in the art. The natural mineral plant nutrient particle size in either dry powder or wet solution, preferably has a Blaine value of approximately 1,000 to approximately 10,000, more preferably approximately 3,500 to approximately 10,000, most preferably approximately 4,500 to approximately 10,000, especially approximately 6,000 to approximately 10,000. The natural mineral plant nutrient particle size in either dry powder or wet solution, preferably has a Blaine value of greater than or equal to approximately 10,000. The foregoing ranges include all of the intermediate values. As the natural mineral plant nutrient particle size in either dry powder or wet solution, is ground to the desired particle size, such as in the micronizing mill 18, a suitable grinding aid can be used. The finished natural mineral plant nutrient particle size in either dry powder, that is collected from the particle size classifier 22 can be transported to the storage silo 26 using an enclosed or sealed screw conveyor 28 of a desirable diameter and length or if wet processed the aqueous solution can be pumped and stored into a storage tank. Alternatively, a series of pipes and nozzles can be attached to the screw conveyer housing along the length thereof, preferably in multiple rows around the radial section of it, so that other plant nutrients may be added if desired such as nitrogen or $CO_2$, can be injected into the conveyor housing as the natural mineral nutrient powder travels thorough the conveyer. Thus, the ground natural mineral nutrient powder is exposed to $CO_2$, nitrogen or some other primary plant nutrient may be added as it travels from the particle classifier 22 to the storage silo 26. It is also desirable that the screw conveyer assembly is sufficiently sealed so that the $CO_2$ and/or nitrogen is retained therein to be mixed or blended with the natural mineral plant nutrient particle size in either dry powder or wet solution. It is also desirable that the $CO_2$ and/or nitrogen is delivered at a pressure sufficient to thoroughly penetrate through the moving body of powder so that between the pressure of the gas being fed into the screw conveyer nozzles and the movement of the screw conveyer that the nitrogen and/or $CO_2$ is dispersed throughout the powder and makes contact with the surface of the particles of the natural mineral plant nutrient particle size powder.

In another embodiment the natural mineral nutrient powder can be mixed with carbon dioxide and a carbon nanomaterial. Graphite nanoplatelets (GP), carbon nanofibers (CNF), activated carbons (ACs), carbon nanotubes (CNTs) and similar carbon nanomaterials have a high surface area and porosity of various nanostructures with high gas adsorption properties. Due to high porosity these materials have a high adsorption rate of gases, therefore nitrogen can be adsorbed into these materials structure. Graphene, a new class of carbon nanomaterials, is found to be economical and has novel properties similar to CNTs. Anyone of these types of carbon nanomaterials can be mixed with carbon dioxide and the natural mineral nutrient powder in conveyer 28. Alternatively, carbon nanomaterials impregnated with carbon dioxide prior to mixing with the natural mineral nutrient powder can also be mixed or blended with the natural mineral nutrient powder having the chemical and physical properties described above. Therefore, these materials allow a high amount of carbon dioxide to be stored on the surface of the natural mineral nutrient and delivered into the concrete mix to farther react with the uncarbonated Ca, Mg, Fe, Na, K and the like. The microporous materials can be exposed to $CO_2$ prior to combining them with the hyaloclastite plant nutrient. In other words, the microporous materials can adsorb or be embedded with $CO_2$ at a $CO_2$ capture facility then sent to be combined with the hyaloclastite at the plant nutrient processing plant. Alternatively, the microporous materials and hyaloclastite plant nutrient can be combined and then exposed to $CO_2$.

As used herein, the term "exposed" to $CO_2$ or "injected" means $CO_2$ in gaseous, solid or liquid form. In gaseous form, the $CO_2$ is in a concentrated form; i.e., at a concentration higher than found in air at standard temperature and pressure or greater than 0.04% by weight or volume as of the filing date of the present application; preferably 4% to 100% $CO_2$ by weight or volume, more preferably 10% to 100% $CO_2$ by weight or volume. The foregoing range includes all of the intermediate values. The $CO_2$ can be obtained from carbon capture processes or an industrial manufacturing or combustion process. When $CO_2$ concentration is less than 100%, the $CO_2$ can be combined with any other gases found in the earth's atmosphere, or in an exhaust gas, such as oxygen, nitrogen and the like in various concentrations. Exhaust gases from various industrial manufacturing or combustion processes containing $CO_2$ level in various amounts are suitable for use in accordance with the present invention As stated above, $CO_2$ is added during the grinding process or it can be added in a post-grinding process in a separate chamber, such as the storage silo 26, where the hyaloclastite plant nutrient of the desired particle size is blended or mixed with $CO_2$ at a desirable temperature and pressure. In particular $CO_2$ in gaseous, liquid or solid form can be added to the grinding process similarly to a grinding aid.

In another disclosed embodiment, the present invention comprises lava, hyaloclastite, scoria or pumice in powder form. The particle size of the lava, hyaloclastite, scoria or pumice powder is sufficiently small such that the lava, hyaloclastite, scoria or pumice powder has plant nutrient release properties. The lava, hyaloclastite, scoria or pumice powder preferably has a volume-based mean particle size of less than or equal to approximately 100 µm particle size of less than or equal to approximately 60 µm, more preferably less than or equal to 40 µm, more preferably less than or equal to 20 µm, most preferably less than or equal to 15 µm, especially less than or equal to 10 µm, more especially less than or equal to 5 µm. The smaller the particle size for the lava, hyaloclastite, scoria or pumice powder the better. However, there are economic limits for grinding rock to small particle sizes. Those limits are well known by those skilled in the art. The lava, hyaloclastite, scoria or pumice powder preferably has a Blaine value of approximately 1,000 to approximately 10,000, more preferably approximately 3,500 to approximately 10,000, most preferably approximately 4,500 to approximately 10,000, especially approximately 6,000 to approximately 10,000. The lava, hyaloclastite, scoria or pumice powder preferably has a Blaine value of greater than or equal to approximately 10,000. The foregoing ranges include all of the intermediate values.

To achieve the desired particles size, the lava, hyaloclastite, scoria or pumice mineral can be ground using conventional mineral grinding equipment including, but not limited to, a ball mill, a roll mill or a plate mill. A particle size classifier can be used in conjunction with the mill to achieve the desired particle size. Equipment for grinding and classifying hyaloclastite to the desired particle size is commercially available from, for example, F. L. Smidth, Bethlehem, PA; Metso, Helsinki, Finland and others. The ground lava, hyaloclastite, scoria, or pumice powder is then preferably classified by screening the powder with a 120-mesh screen or sieve. Preferably approximately 90% by volume of the lava, hyaloclastite, scoria, or pumice mineral powder passes through a 120-mesh screen, especially approximately 95% by volume of the lava, hyaloclastite, scoria or pumice mineral powder passes through a 120-mesh screen and more especially approximately 100% by volume of the lava, hyaloclastite, scoria or pumice powder passes through a 120-mesh screen. Preferably approximately 90% to approximately 100% by volume of the lava, hyaloclastite, scoria or pumice powder passes through a 120-mesh screen, most preferably approximately 95% to approximately 100% by volume of the lava, hyaloclastite, scoria, or pumice mineral powder passes through a 120-mesh screen, especially approximately 100% by volume of the lava, hyaloclastite, scoria, or pumice mineral powder passes through a 120-mesh screen.

As stated above, nitrogen can be added during the grinding process or it can be added in a post-grinding process in a separate chamber, such as the storage silo 26, where natural mineral nutrient of the desired particle size is blended or mixed with nitrogen at a desirable temperature and pressure. In particular nitrogen in gaseous, liquid or solid form can be added to the grinding process similarly to a grinding aid.

As stated above, grinding aids of various types can be added to the grinding process to improve the energy efficiency and natural mineral nutrient properties as well as binding $CO_2$ to the natural mineral nutrient and/or reacting the $CO_2$ with uncarbonated compounds in the natural mineral nutrient.

Lava, hyaloclastite, scoria or pumice, can be ground in the presence of other plant nutrients to create a blended natural mineral plant nutrient. Alternatively, limestone can be added to the mix during the grinding process or after in any suitable percentage.

Additionally, biological organisms or compounds can be added to improve the cation exchanges and chemical reactions to enhance the plant nutrient exchange or absorption process of the natural mineral plant nutrient. These biological organisms may be bacteria, enzymes or a wide range of proteins capable of favoring the cation exchanges and absorption of other plant nutrients.

Alternatively, and optionally, various types of chemical admixtures can be added to the mineral plant nutrient when mixing with carbonic acids or carbonated water. Such admixtures can have carbonation enhancing properties such as sulfates, alkali, earth alkali-sulfates, amines, alkanolamines, such as for example monoethanolamine (MEA) and diglycolamine (DGA), aliphatic amines, such as triethylenetetramine (TETA) and tetraethylenepentamine (TEPA)) and alcoholamines, such as diisopropanolamine (DIPA), diethanolamine (DEA), methyldiethanolamine (MDEA), triethanolamine (TEA) and triisopropanolamine (TIPA)), In addition, proteins or enzymes that can enhance the mineral plant nutrient absorption or adsorption of $CO_2$ or carbonation aids that can accelerate carbon mineralization can be mixed in with the plant nutrient and the carbonated water, carbonic acid or carbon dioxide. A protein that coats the mineral particle so that it binds, absorbs, adsorbs or otherwise stores $CO_2$ on the particle surface and accelerates carbonation can be used. Peptides, carbonic anhydrase, barnacle cement protein, cement proteins can also be used. Six barnacle-specific cement proteins (CPs) have been identified, four of which are thought to be interface proteins, CP19k, -20 k, -43 k, and -68 k, and two bulk proteins, CP52k and CP100k. Barnacle-specific CPs are those proteins that share no homology with any other marine adhesive proteins or any other proteins. Soy protein can be used in a ratio of 0.05-1.5% by weight to the plant nutrient during the mixing of plant nutrient and the carbon dioxide, carbonated water or carbonic acid.

Micro-organisms that have the capacity to produce carbonates through its metabolic activity to improve the carbonation process can also be used. In nature, a lot of bacteria are capable of precipitating calcite ($CaCO_3$) and potentially other carbonates. According to the way calcium carbonate is produced, the generally used bacteria can be primarily categorized into two types, i.e., urease bacteria and non-urease bacteria. Various urease bacteria exist in nature, among which *Bacillus pasteurii, Bacillus aerius, Bacillus sphaericus, Sporosarcina aquimarina, Bacillus megaterium*, etc. are frequently proposed for the self-healing concrete. *Bacillus pasteurii*, a Gram-positive bacterium isolated from soil, can grow normally at temperatures ranging from 15 to 37° C. The urease activities of *Bacillus pasteurii* is outstanding, which can rapidly decompose urea in the environment into ammonium and carbonate. *Bacillus megaterium* belongs to Gram-positive bacterium. Its survival and growth temperature interval extends largely between 3 and 45° C. *B. sphaericus*, Gram-positive aerobic bacterium, forms ellipsoidal spores and is able to produce urease to hydrolyzed urea. Bacterial urease can hydrolyze urea, which will cause $CaCO_3$ precipitation and provide improved properties in concrete. In metabolism, urease-catalyzing urea hydrolysis is secreted by urease organisms. The non-urease bacteria, *Bacillus pseudofirmus, Bacillus cohnii, Bacillus halodurans, Bacillus* mucilaginous L3, *Enterococcus faecalis, Geobacillus stearothermophilus, Bacillus subtilis*, etc., are widely studied as non-urease bacteria inducing calcium carbonate precipitation. *Bacillus subtilis* is a Gram-positive bacterium that forms oval or cylindrical spores. Numerous *Bacillus subtilis* are used in agriculture and in some medicines, therefore it is not detrimental to human health. The *Bacillus pseudofirmus* hydrolyze urea into $NH_3$ and $CO_2$ by using urease produced by themselves. For non-urease bacteria, they will transform organic acids to form calcium carbonate precipitates through their own vital activities under oxygen-containing conditions. Calcium lactate or calcium acetate are often added to nutrients that non-urease bacteria can eventually convert to calcium carbonate. Most microorganisms are intolerant to alkaline environments. The *Bacillus pseudoadamentosa* has an exceptional ability to adapt to the alkaline conditions where the surviving pH value can be up to 11.0. At 10 pH conditions, the growth of *Bacillus pseudofirmus* is fast, indicating the most alkali-resistant behavior. The microporous structure of the mineral powder can provide adequate room and sustain excellent connectivity for the growth and metabolism of microorganisms. Meanwhile, the comparatively thick surface can reduce the penetration of high alkali substances, which can significantly increase the tolerance of concrete bacteria. *Bacillus pasteurella* was found to survive high pH of 12 with the protection of zeolite and to produce calcium carbonate crystals.

In another embodiment the hyaloclastite mineral powder can be mixed with carbon dioxide and water or carbonic acid and a zeolite, such as a natural zeolite or a man-made zeolite, that have a high surface area and porosity of various nanostructures with high gas adsorption properties. Due to high porosity these materials have a high adsorption rate of gases, therefore $CO_2$ can be adsorbed on these material structures. Any one of these types of zeolites can be mixed with carbon dioxide and the mineral powder in the grinding mill and ground together or they can be mixed in the conveyer 28. Alternatively, zeolites impregnated with carbon dioxide prior to mixing with the mineral powder can also be mixed or blended with the mineral powder having the chemical and physical properties described above. Therefore, these $CO_2$ adsorbent materials allow a high amount of carbon dioxide to be stored on the surface of the hyaloclastite mineral plant nutrient and delivered into the soil mix to further react with the uncarbonated Ca, Mg, Fe, Na, K and the like.

Zeolites can be natural or synthetic and are composed of reactive $SiO_2$ and $Al_2O_3$ in its composition. There are more than 50 natural zeolite minerals and 150 synthetic ones are known and used in different industries today. Natural zeolites are hydrated aluminosilicates that occur mainly in altered volcanic tuffs. Natural zeolites are found distributed in deposits around the world. Natural zeolites have generally been considered low quality material because they are a mineral with a heterogeneous composition with different physical and chemical properties. Due to volcanic origin and because of alteration and weathering, zeolite deposits can contain substantial amounts of clays, feldspars or glass. Zeolites consist of an open silica framework, for which alumina can substitute in variable proportions, whereas exchangeable alkaline and alkaline-earth metals compensate for the resulting charge deficit. An example of zeolite can have the following composition: zeolite of the clinoptilolite-heulandite series (51%), gypsum (13%), albite (17%), biotite (10%) and quartz (9%) and the following chemical composition: $SiO_2$ 59.81%, $TiO_2$ 0.19%, $Al_2O_3$ 14.32%, FeO 1.04%, MgO 0.83%, CaO 5.50%, $Na_2O$ 5.76%, $K_2O$ 1.36%. Other types of natural zeolite are Analcime, Phillipsite, Chabazite, Erionite, Mordenite, Clinoptilolite with various amount and ratios of $SiO_2$ and $Al_2O_3$ as well as other elements among them carbonatable elements. Zeolites with a Si/Al ratios higher than about 3 are classified as high-silica zeolites, which tend to be more hydrophobic. Zeolites have microporous structures with a typical diameter of 0.3-0.8 nm. Like most aluminosilicates, the framework is formed by linking of aluminum and silicon atoms by oxides. This linking leads to a 3-dimensional network of Si—O—Al, Si—O—Si, and Al—O—Al linkages. The aluminum centers are negatively charged, which requires an accompanying cation. These cations are hydrated during the formation of the materials. The hydrated cations interrupt the otherwise dense network of Si—O—Al, Si—O—Si, and Al—O—Al linkage, leading to regular water-filled cavities. Because of the porosity of the zeolite, the water can exit the material through channels. Because of the rigidity of the zeolite framework, the loss of water does not result in collapse of the cavities and channels. When dried and processed in accordance with the present invention, the micropores found in zeolite can adsorb relatively large amounts of $CO_2$ gas during the processing. Some of the $CO_2$ adsorbed in the zeolite filled micropores can react with the carbonatable minerals or zeolite found in the zeolite composition while most $CO_2$ will be retained either as a gas or liquid deposited in the micropores by capillary condensation. As such the $CO_2$ filled zeolite particles then can be combined with the hyaloclastite and therefore disposed on or adjacent the surface of the hyaloclastite mineral powder particles and used as a delivery vehicle for the $CO_2$ to be present to carbonate the carbonatable elements from the hyaloclastite in the powder form or over time when dissolved in an alkaline or acidic solution such as when added to soil and released over time as the weathering reaction progresses and the zeolite porosity structure dissolves in the soil. In other words, a carbon dioxide embedded zeolite sorbent powder processed in accordance with the present invention can deliver substantially larger amounts of carbon dioxide in close proximity to the hyaloclastite mineral power when placed in a soil mix to mineralize both the carbonatable minerals from the hyaloclastite mineral powder or zeolites contained therein and to react with the alkalis or acids in the respective soils as well as being a $CO_2$ storage vehicle in a sequestered state or a hydroxyl group of such as Ca, Mg, K and Na or any other alkaline solution found in soil or reacting with ground water.

Synthetic zeolite can be used in a similarly way to first adsorb $CO_2$ within its pores are used in the same manner as described above. In addition, when manufacturing a synthetic zeolite, a significantly greater amount of carbonatable minerals or zeolites, such as Ca, Mg, K and Na can be used to design a zeolite with desired chemical and crystalline properties to perform as a delivery vehicle for $CO_2$ combined with a hyaloclastite mineral powder to be used in a soil such as an alkaline or acidic soil.

Synthetic zeolite from a structural group (Nickel-Strunz classification) includes 09.GA.—Zeolites with $T_5O_{10}$ units (T=combined Si and Al)—the fibrous zeolites
    Natrolite framework (NAT): gonnardite, natrolite, mesolite, paranatrolite, scolecite, tetranat rolite
    Edingtonite framework (EDI): edingtonite, kalborsite
    Thomsonite framework (THO): thomsonite-series 09.GB.—Chains of single connected 4-membered rings
    Analcime framework (ANA): analcime, leucite, pollucite, wairakite
    Laumontite (LAU), yugawaralite (YUG), goosecreekite (GOO), monte sommaite (MON)

09.GC.—Chains of doubly connected 4-membered rings
    Phillipsite framework (PHI): harmotome, phillipsite-series
    Gismondine framework (GIS): amicite, gismondine, garronite, gobbinsite
    Boggsite (BOG), merlinoite (MER), mazzite-series (MAZ), paulingite-series (PAU), perlialite (Linde type L framework, zeolite L, LTL)

09.GD.—Chains of 6-membered rings—tabular zeolites
    Chabazite framework (CHA): chabazite-series, herschelite, willhendersonite and SSZ-13
    Faujasite framework (FAU): faujasite-series, Linde type X (zeolite X, X zeolites), Linde type Y (zeolite Y, Y zeolites)
    Mordenite framework (MOR): maricopaite, mordenite
    Offretite-wenkite subgroup 09.GD.25 (Nickel-Strunz, 10 ed): offretite (OFF), wenkite (WEN)
    Bellbergite (TMA-E, Aiello and Barrer; framework type EAB), bikitaite (BIK), erionite-series (ERI), ferrierite (FER), gmelinite (GME), levyne-series (LEV), dachiardite-series (DAC), epistilbite (EPI)

09.GE.—Chains of $T_{10}O_{20}$ tetrahedra (T=combined Si and Al)
    Heulandite framework (HEU): clinoptilolite, heulandite-series
    Stilbite framework (STI): barrerite, stellerite, stilbite-series
    Brewsterite framework (BRE): brewsterite-series Others
    Cowlesite, pentasil (also known as ZSM-5, framework type MFI), tschernichite (beta polymorph A, disordered framework, BEA), Linde type A framework (zeolite A, LTA)

In a further embodiment, the mineral nutrient powder can be blended or mixed with carbon dioxide or carbonic acid and ammonium salts, quinones, such as electrochemically-reduced quinones, or any other type of quinone, metal-organic framework compounds (MOFs), such as MIL-100 (Fe), a Porous Iron Trimesate with a Hierarchical Pore Structure, cyclodextrin based MOFs, cyclic oligosaccharides that are mass-produced enzymatically from starch, porous organic polymers (POPs), covalent-organic frameworks (COFs), carboxylates, and the like. Ionic liquids (ILs) can be ground, mixed or blended with the mineral powder during the milling process, or post milling, such as in the mixing conveyer or the silo. Any other known type of $CO_2$ adsorbent, binder or carbonation accelerant or enhancer can be used in the mill to be ground with the hyaloclastite or blended post-grinding with the mineral powder so that a sufficient or desirable amount of $CO_2$ is placed onto, or into close proximity to, the powder particle's surface to react with the carbonatable minerals during the powder state or as the mineral nutrient powder dissolves into the soil over time such as the weathering process.

Graphite nanoplatelets (GP), carbon nanofibers (CNF), activated carbons (ACs), carbon nanotubes (CNTs) and similar micro-porous carbon, such as activated carbon, or carbon nanomaterials have shown good gas adsorption properties. Due to high porosity, these materials have a high adsorption rate of gases, therefore $CO_2$ can be adsorbed into these materials structure. Graphene, as a new class of carbon nanomaterials, is found to be economical and has novel properties similar to CNTs. Carbon nanomaterials or activated carbon powders impregnated with carbon dioxide can then be mixed or blended with the hyaloclastite plant nutrient having the chemical and physical properties described above. We call all these types of carbon materials microporous carbon materials. Microporous carbon materials can adsorb or be embedded with carbon dioxide separately from the hyaloclastite grinding process and used as a carbon dioxide delivery vehicle to the hyaloclastite mineral powder then mixed with the hyaloclastite mineral powder. Alternatively microporous carbon materials can be used as a grinding aid and fed or injected into the grinding mill while the hyaloclastite is being ground into a fine powder either in the presence of the carbon dioxide or atmospheric air. In other words microporous carbon materials provide an enhanced amount of carbon dioxide on the surface or close proximity to the hyaloclastite particle surface mineral nutrient powder so that the carbon dioxide can react with the carbonatable minerals in the powder state or over time while the mineral powder and the microporous carbon materials are mixed and dissolved in a soil and therefore the carbon dioxide mineralize to carbonatable elements contained in the hyaloclastite mineral powder creating carbonated minerals of various types. Alternatively, the hyaloclastite powder combined with microporous carbon materials can be exposed to carbon dioxide post-grinding at ambient or elevated temperatures, and optionally with steam, in the screw conveyer 22 or in the storage silo 26, such as described in the current invention.

Any one or more of the grinding aids, $CO_2$ sorbents or sorbent enhancers, carbonation enhancers, such as the carbon microporous materials, zeolites, carbonation accelerants and/or $CO_2$ adsorption enhancing compounds and/or steam, or any combination thereof, any aids in the $CO_2$ binding or adsorption process and/or the carbonation process, as described in the present inventions or regardless of the nature of compositions as described in the present invention can be added or blended during the grinding or post-grinding process to enhance the $CO_2$ adsorption, absorption and/or carbonation process during the powder state or the dissolving of the mineral powder in an alkaline or acidic soil over time. We call these elements $CO_2$ adsorption enhancers and/or carbonation accelerants that serve to bind and provide additional amounts of $CO_2$ to the mineral powder either on the surface thereof, or in close proximity thereto, so that it is present to react with the carbonatable elements while in the powder state or once the powder dissolves in a soil solution over time through the weathering process.

Porous organic polymers (POPs) are generally defined as a group of covalent organic porous materials with high porosity made of different elements (carbon, boron, hydrogen, oxygen, and nitrogen) and strong covalent bonds. These organic macromolecules have high specific surface areas, tunable porosities, low densities, high chemical and thermal stabilities, variable compositions, convenient post-functionalization, extended π-conjugations, and their high contents of carbon, nitrogen, oxygen, and other non-metallic atoms. POPs have been classified into four types: covalent triazine frameworks (CTFs), hypercrosslinked polymers (HCPs), covalent organic frameworks (COFs), and conjugated microporous polymers (CMPs). All POPs are amorphous materials-except for a small number of CTFs and COFs that are crystalline materials with ordered structures prepared under thermodynamic control. Like nanoporous materials, POPs have many potential applications because of their high surface areas and uniform pore sizes, with large numbers of channels and active sites available for chemical reactions. Examples of these types of polymers are nitrogen-enriched microporous polymers containing various contents of amino groups through condensation reactions of melamine with formohydrazide, formamide, N,N-dimethylformamide (DMF), and N-methylformamide, 1,2,3-triazolo units; their Tz-CTF polymeric frameworks, hollow microspherical and microtubular carbazole-based COFs through condensations of Car-3NH$_2$ and the triformyl linkers TPA-3CHO, TPP-3CHO, and TPT-3CHO with various degrees of planarity, triarylamine monomers based (TPT-based COFs), (3-ketoenamine-linked COFs (TFP-TPA, TFP-Car, and TFP-TPP) and the like.

The porous organic polymers can adsorb or be embedded with carbon dioxide separately from the hyaloclastite grinding process and used as a carbon dioxide delivery vehicle to the hyaloclastite mineral powder then mixed with the hyaloclastite mineral powder. Alternatively, porous organic polymers can be used as a grinding aid and fed or injected into the grinding mill while the hyaloclastite is being ground into a fine powder either in the presence of carbon dioxide or atmospheric air. In other words these polymers provide an enhanced amount of carbon dioxide on the surface of or in close proximity to the hyaloclastite particle surface mineral powder so that the carbon dioxide can react with the carbonatable minerals in the powder state or over time while the mineral powder and the porous organic polymers are dissolved in an alkaline or acidic soil or solution and therefore the carbon dioxide mineralize the carbonatable elements contained in the hyaloclastite mineral powder creating carbonated minerals of various types. Alternatively, the hyaloclastite powder combined with porous organic polymers can be exposed to carbon dioxide post-grinding at ambient or elevated temperatures, and optionally with steam, in the screw conveyer 22 or in the storage silo 26, such as described in the current invention.

Quinones are a special class of ketones in which carbonyl groups are a part of an aromatic ring of benzene, anthracene, or naphthalene such as ubiquitous biological pigments found in a range of living organisms (bacteria, fungi, higher plants, and in few animals). They exist in nature in many forms such as benzoquinones, naphthoquinones, anthraquinones, and polycyclic quinones. For example, the K vitamins (phylloquinone) are naphthoquinones. Quinones can adsorb or be embedded with carbon dioxide separately from the hyaloclastite grinding process and used as a carbon dioxide delivery vehicle to the hyaloclastite mineral powder then mixed with the hyaloclastite mineral powder. Alternatively, quinones can be used as grinding aids and fed or injected into the grinding mill while the hyaloclastite is being ground into a fine powder either in the presence of the carbon dioxide or atmospheric air. In other words quinones provide an enhanced amount of carbon dioxide on the surface of or in close proximity to the hyaloclastite particle or mineral powder surface so that the carbon dioxide can react with the carbonatable minerals in the powder state or over time while the mineral powder and the quinine are dissolved in an alkaline or acidic soil solution and therefore the carbon dioxide mineralize to carbonatable elements contained in the hyaloclastite mineral powder creating carbonated minerals of various types while releasing the balance of its plant nutrient elements to be used as plant nutrients. Alternatively, the hyaloclastite powder combined with quinones can be exposed to carbon dioxide post-grinding at ambient or elevated temperatures, and optionally with steam, in the screw conveyer 22 or in the storage silo 26, such as described in the current invention.

Ionic liquids (IL) are salts in the liquid state. In some contexts, the term has been restricted to salts whose melting point is below a specific temperature, such as 100° C. (212° F.). The ionic bond is usually stronger than the Van der Waals forces between the molecules of ordinary liquids. Because of these strong interactions, salts tend to have high lattice energies, manifested in high melting points. Some salts, especially those with organic cations, have low lattice energies and thus are liquid at or below room temperature. Examples include compounds based on the 1-ethyl-3-methylimidazolium (EMIM) cation and include: EMIM:Cl, EMIMAc (acetate anion), EMIM dicyanamide, $(C_2H_5)(CH_3)C_3H_3N^+2\cdot N(CN)^-_2$, that melts at −21° C. and 1-butyl-3,5-dimethylpyridinium bromide which becomes a glass below −24° C. In particular room-temperature ionic liquids (RTILs) are dominated by salts derived from 1-methylimidazole, i.e., 1-alkyl-3-methylimidazolium. Examples include 1-ethyl-3-methyl-(EMIM), 1-butyl-3-methyl-(BMIM), 1-octyl-3 methyl (OMIM), 1-decyl-3-methyl-(DMIM), 1-dodecyl-3-methyl-docecyl (MIM). Other imidazolium cations are 1-butyl-2,3-dimethylimidazolium (BMMIM or DBMIM) and 1,3-di(N,N-dimethylaminoethyl)-2-methylimidazolium (DAMI). Other N-heterocyclic cations are derived from pyridine: 4-methyl-N-butyl-pyridinium (MBPy) and N-octylpyridinium (C8Py). Conventional quaternary ammonium cations also form ILs; e.g., tetraethylammonium (TEA) and tetrabutylammonium (TBA). Ionic Liquids can adsorb or be embedded with carbon dioxide separately from the hyaloclastite grinding process and used as a carbon dioxide delivery vehicle to the hyaloclastite mineral powder then mixed with the hyaloclastite mineral powder. Alternatively, ionic liquids can be used as grinding aids and fed or injected into the grinding mill while the hyaloclastite is being ground into a fine powder either in the presence of carbon dioxide or atmospheric air. In other words ionic liquids provide an enhanced amount of carbon dioxide on the surface of or in close proximity to the hyaloclastite particle or mineral powder surface so that the carbon dioxide can react with the carbonatable minerals in the powder state or over time while the mineral powder and the Ionic Liquid are dissolved in an alkaline or acidic soil solution and therefore the carbon dioxide mineralizes to carbonatable elements contained in the hyaloclastite mineral powder creating carbonated minerals of various types while releasing the plant nutrient contained therein. Alternatively, the hyaloclastite powder coated with ionic liquids can be exposed to carbon dioxide post-grinding at ambient or elevated temperatures, and optionally with steam, in the screw conveyer 22 or in the storage silo 26, such as described in the current invention.

Covalent organic frameworks (COFs) are a type of organic crystalline porous material, prepared through reticular chemistry with building blocks featuring light elements (such as C, H, O, N, or B atoms), and connected through covalent bonds and extended in two or three dimensions. Examples of covalent organic frameworks are based on the condensations of widely used types of linkages in COFs such as boroxine, boronic ester, imine, hydrazone, azine, β-ketoenamine, imide, borazine, 1,4-dioxin, C=C bond, phenazine, triazine, urea, squaraine, and double-linkage. The chemical stability of covalent organic frameworks can be improved with the synthesis of β-ketoneamines from 1,3,5-triformylphloroglucinol (TFP-3OHCHO) and primary amines, through irreversible enol-keto tautomerization, creating robust networks that resist strong acids and bases. Covalent organic frameworks can adsorb or be embedded with carbon dioxide separately from the hyaloclastite grinding process and used as a carbon dioxide delivery vehicle to the hyaloclastite mineral powder then mixed with the hyaloclastite mineral powder. Alternatively, covalent organic frameworks can be used as grinding aids and fed or injected into the grinding mill while the hyaloclastite is being ground into a fine powder either in the presence of the carbon dioxide or atmospheric air. In other words, covalent organic frameworks provide an enhanced amount of carbon dioxide on the surface of or in close proximity to the hyaloclastite particle or mineral powder surface so that the carbon dioxide can react with the carbonatable minerals in the powder state or over time while the mineral powder and the covalent organic framework are dissolved in an alkaline or acidic soil solution and therefore the carbon dioxide mineralizes to carbonatable elements contained in the hyaloclastite mineral powder creating carbonated minerals of various types. Alternatively, the hyaloclastite powder coated with covalent organic frameworks can be exposed to carbon dioxide post-grinding at ambient or elevated temperatures, and optionally with steam, in the screw conveyer 22 or in the storage silo 26, such as described in the current invention.

Metal-organic frameworks (MOFs) are organic-inorganic hybrid crystalline porous materials that consist of a regular array of positively charged metal ions surrounded by organic "linker" molecules. The metal ions form nodes that bind the arms of the linkers together to form a repeating, cage-like structure. Due to this hollow structure, MOFs have an extraordinarily large internal surface area and can adsorb or embed significant amounts of carbon dioxide in its pore structure. So far, more than 90,000 different MOF structures have been reported and over 500,000 are predicted to be possible. Metal Organic Frameworks (MOFs) constitute a class of solid porous materials, which consist of metal ions or metallic clusters, which act as nodes, and polydentate organic ligands, which act as linkers between the nodes. The metal nodes (metal ions or metallic clusters) act as connection points and the organic ligands bridge the metal centers through coordination bonds, thus, forming networks of one-dimension, two-dimensions, or three-dimensions. The main structural features of the MOFs, which are directly related to their properties and applications, are the high porosity, the large volume of the pores, which can reach the 90% of the crystalline volume or more, the large specific surface area (several thousand $m^2 \cdot g^{-1}$), and the high thermal stability (250-500° C.) due to the presence of strong bonds (e.g., C—C, C—H, C—O, and M-O). Examples of MOFs are Isoreticular Metal Organic Frameworks (IRMOFs), such as IRMOF-3 containing 2-amino-1,4-benzenedicarboxylic acid can undergo chemical modification with a diverse series of anhydrides and isocyanates yielding isostructural MOFs containing different functional groups, MOF-74-Mg, which is the magnesium analogue of MOF-74, shows the highest $CO_2$ uptake capacity of 228 and 180 $cm^3 \cdot g^{-1}$ at 273 and 298 K and 1 bar, respectively, MOF-74-Mg, MOF-210 has a very high surface area of 10,450 $m^2 \cdot g^{-1}$ and shows a $CO_2$ uptake value of 2400 $mg \cdot g^{-1}$ (74.2 wt %, 50 bar at 298 K), MOF-177 or MIL-101(Cr) (60 wt % and 56.9 wt %, respectively), MOF-200, MOF-210 under similar conditions. Other MOFs, which show considerably higher $CO_2$ uptake compared with other solid materials, are the NU-100 (69.8 wt %, 40 bar at 298 K), the MOF-5 (58 wt %, 10 bar at 273 K), HKUST-1 (19.8 wt %, 1 bar at 298 K), MIL-100(Fe), a Porous Iron Trimesate with a Hierarchical Pore Structure, cyclodextrin based MOFs, IRMOF-74-III-CH$_2$NH$_2$, IRMOF-74-III-CH$_2$NHMe, carbamic types and the likes.

Metal-organic frameworks can adsorb or be embedded with carbon dioxide separately from the hyaloclastite grinding process and used as a carbon dioxide delivery vehicle to the hyaloclastite mineral powder when mixed with the hyaloclastite mineral powder. Alternatively, Metal-organic frameworks can be used as grinding aids and fed or injected into the grinding mill while the hyaloclastite is being ground into a fine powder either in the presence of carbon dioxide or atmospheric air. In other words, Metal-organic frameworks provide an enhanced amount of carbon dioxide on the surface of or in close proximity to the hyaloclastite particle or mineral powder surface so that the carbon dioxide can react with the carbonatable minerals in the powder state or over time while the mineral powder and the MOFs are dissolved in an alkaline or acidic soil solution and therefore the carbon dioxide mineralizes to carbonatable elements contained in the hyaloclastite mineral powder creating carbonated minerals of various types. Alternatively, the hyaloclastite powder combined with Metal-organic frameworks can be exposed to carbon dioxide post-grinding at ambient or elevated temperatures, and optionally with steam, in the screw conveyer 22 or in the storage silo 26, such as described in the current invention.

Polymer brushes are special macromolecular structures with polymer chains densely tethered to another polymer chain (one-dimensional, 1D) or the surface of a planar (two-dimensional, 2D), spherical or cylindrical (three-dimensional, 3D) solid via a stable covalent or noncovalent bond linkage. In comparison with the corresponding linear counterpart with similar molecular composition, one-dimension polymer brushes have some fascinating properties including wormlike conformation, compact molecular dimension, and notable chain end effects due to their compact and confined densely grafted structure. Polymer brushes are composed of long macromolecules that are anchored by one chain-end to a surface at a density that is high enough such that the polymers stretch out, away from the surface. These brushes have become popular surface modifications in the development of adsorbent surfaces. As such, they can be broadly applied, ranging from (bio) medical materials to membrane technologies. Moreover, polymers are responsive to small changes in their environment, such as temperature, pH, or solvent composition. A polymer brush is a coating comprised of polymer chains, end-anchored to a substrate at a high areal density. These brushes can be composed of negatively charged anionic or positively charged cationic polyelectrolytes, zwitterionic polymers and neutral macromolecules or copolymers containing different types of monomers. Individually, surface-anchored polymers behave comparably to free polymers, assuming conformations that minimize their free energy, which consists of contributions from solvent, substrate, and polymer-polymer contacts, and the conformational entropy of the chain. In the simplest case, this is a "mushroom": a surface-anchored analogue to the coil and globule states found in free polymers. Under poor solvent conditions, however, the most favorable conformation is often a "pancake" state in which the polymer backbone adsorbs to the grafting surface. When the density of polymers on the surface becomes sufficiently high, the polymers start to overlap and volume interactions cause the chains to stretch away from the surface. This structure of "bristles" extending away from the substrate gives the polymer brush its name. The properties of polymer brushes alter in response to their environment as well, which has been utilized to control adhesion and friction, channel flow, drug release, and more. The monolithic materials are studied in terms of porosity and structure to investigate the $CO_2$ adsorption and how the capacity is affected by the initial particles compared with the ones with polymer brushes. Polymer brushes can be synthesized from any number of polymers among them poly(acrylic acid) (PAA), poly(vinyl caprolactam) (PVCL), and poly[(2-(methacryloyloxy)ethyl) trimethylammonium chloride] (PMETAC) A range of composite monoliths can be synthesized—rGO monolith (G), rGO/$CeO_2$ (GCe), rGO/CeO2/PAA (GCePA), rGO/$CeO_2$/PVCL (GCePV), and rGO/$CeO_2$/PMETAC (GCePM)—that offers the possibility to study the effect of different functional polymers inside a monolith on the $CO_2$ adsorption. The use of polymer brushes with different responses in different environments, such as pH, can show other aggregations of the particles with the polymer brushes. Thus, it can also affect the preparation of the monolith with the addition of particles with different functionalities and responses. Polymer brushes can be grafted on to the surface of the hyaloclastite to enhance the $CO_2$ adsorption properties and store an enhanced quantity of $CO_2$ of the surface of the hyaloclastite plant nutrient surface. The polymer to create the polymer brushes can be added to the hyaloclastite during grinding or post-grinding in any suitable quantity to create an enhanced $CO_2$ adsorption surface on the hyaloclastite particle surface.

The foregoing materials that have high surface areas and/or high porosity and are used as delivery vehicles for placing $CO_2$ on the surface of or in close proximity to the hyaloclastite particle or mineral powder surface are preferably combined with the hyaloclastite or mineral powder in amounts of approximately 0.1% to approximately 40% by weight, more preferably approximately 1% to approximately 30% by weight, especially approximately 5% to approximately 20% by weight. The foregoing ranges include all of the intermediate values. The hyaloclastite can be combined with any one or more of the above at any temperature or pressure suitable to the process. It can be combined at ambient, sub-ambient or above ambient temperature. The elevated temperature preferably can be in the range of 30° C. to 250° C. The optional steam use is to provide heat and moisture to facilitate the binding of the $CO_2$, the carbonation accelerant and/or $CO_2$ adsorption enhancing compound or any combination thereof with the mineral powder as described above. Steam is preferably used to provide the appropriate and desired amount of moisture between approximately 4% and approximately 40%, with a temperature of approximately 50 to approximately 250° C. (the foregoing moisture and temperature range includes all of the intermediate values). It can be combined at a sub-atmospheric, atmospheric or above atmospheric pressures.

The foregoing discussion of carbon dioxide absorption enhancing materials was described in combination with hyaloclastite. However, it is also contemplated that the carbon dioxide absorption enhancing materials can be used in combination with lava, scoria, volcanic ash and pumice and having the chemical compositions as described herein.

In one disclosed embodiment of the present invention, the lava, hyaloclastite, scoria or pumice preferably has a chemical composition of approximately 40% to approximately 65% by weight $SiO_2$, approximately 10% to approximately 18% by weight $Al_2O_3$, 4% to approximately 20% by weight CaO, approximately 3% to approximately 15% by weight MgO, approximately 4% to approximately 18% by weight $Fe_2O_3$. In addition to the foregoing, other compounds can be present in small amounts, such as $K_2O$, $TiO_2$, $P_2O_5$, MnO, various metals, rare earth trace elements and other unidentified elements. When combined, these other compounds represent less than 10% by weight of the total chemical composition of the lava, hyaloclastite, scoria or pumice mineral.

In another disclosed embodiment, the lava, hyaloclastite, scoria or pumice in accordance with the present invention preferably has a density or specific gravity of approximately 2.4 to approximately 3.1.

Lava, hyaloclastite, scoria or pumice in accordance with the present invention can be in crystalline or amorphous (glassy) form and is usually found as a combination of both in varying proportions. Preferably, the lava, hyaloclastite, scoria, or pumice in accordance with the present invention comprises approximately 0% to 100% by weight amorphous form, more preferably approximately 10% to approximately 80% by weight amorphous form, most preferably approximately 20% to approximately 60% by weight amorphous form, especially approximately 30% to approximately 50% by weight amorphous form. Preferably, the basaltic hyaloclastite and the intermediate basaltic hyaloclastite comprise approximately 10% to 100% by weight amorphous form, more preferably approximately 20% to 100% by weight amorphous form, most preferably approximately 30% to 100% by weight amorphous form, especially approximately 40% to 100% by weight amorphous form, more especially approximately 50% to 100% by weight amorphous form and most especially approximately 60% to 100% by weight amorphous form. The crystalline portion of lava, hyaloclastite, scoria or pumice preferably comprises approximately 3% to approximately 20% by weight olivine, approximately 5% to approximately 40% by weight clinopyroxene, approximately 5% to approximately 60% by weight plagioclase, and approximately 0% to approximately 40% (or less than 40%) by weight other minerals including, but not limited to, magnetite, UlvoSpinel, quartz, feldspar, pyrite, illite, hematite, chlorite, calcite, hornblende, biotite, K-feldspars, mordenite, clinoamphibole, ilmenite hypersthene (an orthopyroxene), feldspathoids sulfides, metals, rare earth minerals, other unidentified minerals and combinations thereof. The foregoing ranges include all of the intermediate values.

The soil and natural mineral plant nutrient based on volcanic mineral and soil or mixtures thereof in accordance with the present invention can be combined physically or mechanically in any suitable manner and is not a critical feature of the present invention. For example, the lava, hyaloclastite, scoria or pumice or mixtures thereof in accordance with the present invention can be mixed together in powder form by spreading the natural mineral plant nutrient on the ground then mechanical implements mix or combine it with the soil. Alternatively, the mineral plant nutrient according to this invention can be combined with water and sprayed on the soil with mechanical implements from a tank. Similarly, the mineral plant nutrient according to this invention can be combined with irrigation water and sprayed on the soil through the irrigation channels or pipes. Also, the mineral plant nutrient according to this invention can be combined with water and sprayed directly on the plant body or leaves with mechanical implements from a tank. The mineral plant nutrient according to this invention can also be pelletized in small pellets, prills or granules that can be spread using mechanical implements and mixed or combined with the soil. Alternatively, the hyaloclastite mineral powder or mineral mixture or hyaloclastite mineral or mineral mixture containing $CO_2$ impregnated with one or more of the microporous carbon, carbon nanotubes, zeolites, amines, enzymes, protein, amino acids, bacteria, metal-oxide frameworks, ionic liquids and the like in accordance with the present invention can be formed into a pellet, a granule or a prill, The methods and machinery to form powdered minerals into pellets, granules or prills is well known in the art. The pellets, granules or prills are preferably approximately ⅛ inch to ¼ inch in size and are preferably applied at a rate of approximately 100 to 500 pounds per acre. The process and equipment for forming fertilizer pellets, prills and granules is well known to those skilled in the art.

The minerals with the chemical composition provide the plant secondary nutrients and micronutrients when reduced to fine particle size. In addition, based on the Jackson Weathering index, the minerals selected for the mineral plant nutrient are the most weatherable with the index 2, 3, 4 and 5. When reduced to fine particle size these will weather more rapidly and particularly in the four types of soils mentioned in the summary of the invention. That means that when the mineral is in a crystalline form those crystals are on the index of 2-5 of easiest to breakdown into the element it's made of. However, for the minerals that are amorphous, the glassy state is the fastest weatherable state and the plant nutrient elements contained therefore are released even faster into the soil and especially when combined with the soil types mentioned in the summary of the invention.

The mineral plant nutrient according with the present invention chosen from a volcanic mineral of basaltic, intermediate or andesitic chemistry will have most of the elements considered as a secondary plant nutrient (Calcium, Magnesium and to some extend Sulfur) as well as most of the Micronutrients such as Boron (B), Chlorine (Cl), Cobalt (Co), Iron (Fe), Manganese (Mn), Molybdenum (Mo), Zinc (Zn), Nickel (Ni), Copper (Cu), in various quantities. The mineral plant nutrient having a mean particle size of less than or equal to 60 microns, of silt and clay size fraction, when mixed with soil and water allows the release of the composing elements to be released to the plant roots to be used as plant nutrients. Additionally, hyaloclastite in the fine sand fraction between 60 micron and 150 micron particle size can be mixed with the silt or clay fraction size hyaloclastite or soils. The sand fraction will allow more air in the soil while taking longer to breakdown by weathering into the silt and clay fraction. The finer the particle size the closer to the clay size fraction the faster the reaction with the soil to breakdown the elements into the soil for use by the plant roots. This is the case when the volcanic mineral is of crystalline make up, such as basaltic, intermediate or andesitic lava or of hyaloclastite where the volcanic mineral has a higher amorphous content. However, the volcanic mineral with higher amorphous content will breakdown and weather faster than the crystalline material in an alkaline or basic soil. If a crystalline volcanic mineral is desired for use for accelerated element breakdown, then the particle size can be reduced farther or used in acidic type soils. A smaller particle size will breakdown and release elements and nutrients faster than a coarser particle size. For example, sand grains coarser than 150 microns may take too long of a time to breakdown will not be suitable for a plant nutrient with a seasonal growing cycle, however this size fraction will weather in a multiyear cycle. In the case of a volcanic mineral with higher amorphous content this can be in a potentially coarser fraction such as the 100 microns mean particle size. If the mineral plant nutrient is used in plant growth in warm climates, then a coarser particle size will do. However, if the mineral plant nutrient is used in a cold climate, then a much finer particle size would be needed.

The mineral plant nutrient can be mixed with soil in general or it can be added and mixed with soil only around the plant root system either in the field or in a greenhouse when seeds are potted and plants are later transplanted into normal soil in the field. In particular the mineral plant nutrient is designed to work well in initial seed planting where the plant is grown to certain size in a pot then transplanted into normal soil. The application of the natural mineral plant nutrients in the field can be targeted to the plant roots systems and not the overall field application. To deliver the natural mineral plant nutrient to the plant root system the mineral plant nutrient can be injected or sprayed into the ground around the plant be conventional means.

Another way to deliver the mineral plant nutrient in accordance with the present invention is to coat the surface of plant seeds with the mineral plant nutrient. In order to coat the surface of plant seeds the mineral plant nutrient can be suspended in an aqueous solution containing enzymes or starches or other known sticker materials known in the art that allow the powder like mineral plant nutrient to stick to the surface of the seed. Alternatively, the mineral plant nutrient can be suspended in a water-soluble polymer that then can be applied to the exterior surface of the plant seed. As such when planted the mineral plant nutrient is present at the seed germination stage and activated by water. It is then valuable to provide secondary and micro nutrients to the plant from the very early germinating stage on to the initial root development stage and later.

In another disclosed embodiment, the present invention comprises a soil such as an alkaline or acidic soil combined with hyaloclastite, lava, scoria, volcanic ash or pumice or mixtures thereof in accordance with the present invention. Preferably, the alkaline soil and rain water form an alkaline solution with a pH between 8-12 and hyaloclastite, lava, scoria, volcanic ash or pumice powder or mixtures thereof, more preferably, volcanic ash or pumice or mixtures thereof having a volume-based mean particle size of less than or equal to approximately 100 µm, most preferably hyaloclastite, volcanic ash or pumice or mixtures thereof having a volume-based mean particle size of less than or equal to approximately 60 µm, especially less than or equal to approximately m, more especially less than or equal to approximately 30 µm, most especially less than or equal to approximately 15 µm. The foregoing ranges include all of the intermediate values. In simple terms the carbon dioxide disposed on the surface of the hyaloclastite mineral powder particles when delivered into the soil, forms an alkaline solution that will dissolve the hyaloclastite powder elements and the carbonatable elements will combine with the carbon dioxide therein to form carbonated minerals among other minerals thereby mineralizing carbon dioxide in soil and other minerals contained therein that can be absorbed by plants to be used as plant nutrients. Alternatively, acidic soil and rain water form an acidic solution with a pH between 3-7 and hyaloclastite, lava, scoria, volcanic ash or pumice or pumice powder or mixtures thereof, preferably, having a volume-based mean particle size of less than or equal to approximately 100 µm, more preferably less than or equal to approximately 60 µm, most preferably less than or equal to approximately 45 µm, especially less than or equal to approximately 30 µm, more especially less than or equal to approximately 15 µam. The foregoing ranges include all of the intermediate values. In simple terms the carbon dioxide disposed on the surface of the mineral powder particles when delivered into the acidic soil, forms an acidic solution that will dissolve the powder elements and the carbonatable elements will combine with the carbon dioxide therein to form carbonated minerals among other minerals thereby mineralizing carbon dioxide in soil and other minerals contained therein that can be absorbed by plants to be used as plant nutrients or mineralize $CO_2$ into the carbonates in the soil.

The mineral plant nutrient in accordance with the present invention can be used as a plant nutrient as described and while it is weathered and broken down into its nutrient elements components it will also break down into the un-carbonated elements that react with $CO_2$ present in the soil and air to create simple or complex carbonate minerals.

The following examples are illustrative of selected embodiments of the present invention and are not intended to limit the scope of the invention.

Example 1

Hyaloclastite is mined from a deposit typically has a particle size of 400 microns to ½ inch. Hyaloclastite in its natural state is therefore introduced to a ball mill and processed to a volume-based mean particle size of approximately 50 microns.

Example 2

The ground hyaloclastite from Example 1 is processed in a granulator machine to produce hyaloclastite granules of approximately ⅛ inch to ¼ inch. The hyaloclastite granules are applied to the surface of a neutral pH soil by broadcasting. The hyaloclastite granules are applied at the rate of approximately 100 to 500 pounds per acre. The soil is tilled with conventional farming equipment. The soil to which the granules are applied is planted with a food crop, such as corn, soy beans or legumes. Water from rain or irrigation is added to the soil and hyaloclastite is dissolved or weathered into the separate plant nutrients and carbonatable elements. Plant nutrients such as K, P, S, B, Co, Cu, Fe, Mo, Zn and Ni are used by the crop plants as nutrients. Carbonatable elements such as Ca, Mg, K, Na and Fe react with $CO_2$ present in the soil and the air to create simple or complex carbonate minerals thereby mineralizing $CO_2$.

Example 3

The same procedure as Example 2 is followed except the ground hyaloclastite is mixed with a primary nutrient, such as urea formaldehyde, before granulation.

Example 4

The ground hyaloclastite from Example 1 is suspended in water with the help of a conventional dispersing agent. The suspension is added to the irrigation water used to irrigate a food crop such as almond trees. Water from rain or irrigation is added to the soil and hyaloclastite is dissolved or weathered into the separate plant nutrients and carbonatable elements Plant nutrients such as K, P, S, B, Co, Cu, Fe, Mo, Zn and Ni are used by the crop plants as nutrients. Carbonatable elements such as Ca, Mg, K, Na and Fe react with $CO_2$ in the ground and from the air to create simple or complex carbonate minerals elements thereby mineralizing $CO_2$.

Example 5

The ground hyaloclastite from Example 1 is processed in a coating machine to coat a plant seed using a water-soluble polymer. The hyaloclastite plant nutrient coated seeds such as corn, soy beans or legumes are planted in a soil by mechanical implements. Water from rain or irrigation is added to the soil and hyaloclastite is dissolved or weathered into the separate plant nutrients and carbonatable elements Plant nutrients such as K, P, S, B, Co, Cu, Fe, Mo, Zn and Ni are used by the crop plants as nutrients. Carbonatable elements such as Ca, Mg, K, Na and Fe react with $CO_2$ in the ground and the air to create simple or complex carbonate minerals thereby mineralizing $CO_2$.

Example 6

Volcanic mineral as mined from a deposit typically may have a particle size of 80 micron—¼ inch. Volcanic mineral is then screened using a vibrating mesh screener to a volume-based mean particle size of 100 micron.

Example 7

The screened volcanic mineral from Example 6 is spread on top of a soil with the help of a conventional fertilizer spreading farming equipment. The soil is then tilled using a conventional farming equipment and then a food crop such as almond trees or legumes, such as cabbage, beets, spinach or other leafy green field crop is planted. Water from rain or irrigation is added to the soil and hyaloclastite is dissolved or weathered into the separate plant nutrients and carbonatable elements Plant nutrients such as K, P, S, B, Co, Cu, Fe, Mo, Zn and Ni are used by the crop plants as nutrients. Carbonatable elements such as Ca, Mg, K, Na and Fe react with $CO_2$ in the ground and the air to create simple or complex carbonate minerals thereby mineralizing $CO_2$.

Example 8

Hyaloclastite is processed in the same manner as described in Example 1 above. The combination of a microporous carbon material and hyaloclastite from the storage silo 26 is blended with an alkaline or basic soil. The soil is tilled and a crop is planted. Water from rain or irrigation is provided to the soil and the hyaloclastite react with the alkaline soil solution releasing nutrients and carbonatable minerals. Water from rain or irrigation is added to the soil and hyaloclastite is dissolved or weathered into the separate plant nutrients and carbonatable elements Plant nutrients such as K, P, S, B, Co, Cu, Fe, Mo, Zn and Ni are used by the crop plants as nutrients. Carbonatable elements such as Ca, Mg, K, Na and Fe react with $CO_2$ stored in the microporous materials or from in the ground and the air to create simple or complex carbonate minerals thereby mineralizing $CO_2$. The plant nutrients are absorbed by the crop and the carbonatable mineral released from the hyaloclastite react with $CO_2$ in the ground. The $CO_2$ adsorbed on the microporous carbon is mineralized within the soil by carbonating the carbonatable elements Example 9

Hyaloclastite is processed in the same manner as described in Example 1 and 6 above. The hyaloclastite from example 1 and 6 are combined together then spread on an alkaline or basic soil. The soil is tilled and a crop is planted. Water from rain or irrigation is added to the soil and hyaloclastite is dissolved or weathered into the separate plant nutrients and carbonatable elements. Plant nutrients such as K, P, S, B, Co, Cu, Fe, Mo, Zn and Ni are used by the crop plants as nutrients. Carbonatable elements such as Ca, Mg, K, Na and Fe react with CO2 in the ground and the air to create simple or complex carbonated mineral thereby mineralizing $CO_2$.

Example 10

Hyaloclastite is processed in the same manner as described in Example 1 and 6 above. A microporous carbon material is exposed to carbon dioxide, such as the flue gas from an industrial combustion process, such as the flue gas from a cement kiln. The hyaloclastite from example 1 and 6 are combined together and further combined with the microporous carbon material embedded with $CO_2$ and the combined hyaloclastite and microporous material from the storage silo 26 is then blended with an alkaline or basic soil. The soil is tilled and a crop is planted. Water from rain or irrigation is provided to the soil and the hyaloclastite reacts with the soil solution releasing nutrients and carbonatable minerals. The plant nutrients are absorbed by the crop and the carbonatable minerals released from the hyaloclastite react with $CO_2$ in the ground, air and from the microporous material. Elements weathered into the separate plant nutrients and carbonatable elements. Plant nutrients such as K, P, S, B, Co, Cu, Fe, Mo, Zn and Ni are used by the crop plants as nutrients. Carbonatable elements such as Ca, Mg, K, Na and Fe react with $CO_2$ in the ground and the air to create simple or complex carbonated mineral, thereby mineralizing $CO_2$. The $CO_2$ adsorbed on the microporous carbon reacts with the carbonatable elements as the plant nutrient is weathered and elements are dissolved in soil are mineralized within the soil by carbonating the carbonatable elements.

Example 11

Hyaloclastite is processed in the same manner as described in Example 1 above, except it is exposed to carbon dioxide gas during the grinding process. The carbon dioxide gas comes from the flue gas from a cement kiln. The hyaloclastite absorbs/adsorbs carbon dioxide during the grinding process. The hyaloclastite from the storage silo 26 is then blended with an alkaline or basic soil. The soil is tilled and a crop is planted. Water from rain or irrigation is provided to the soil and the hyaloclastite reacts with the soil solution releasing nutrients and carbonatable minerals. The plant nutrients are absorbed by the crop and the carbonatable minerals released from the hyaloclastite react with $CO_2$ absorbed/adsorbed on the hyaloclastite as well as in the ground and air. Elements weathered into the separate plant nutrients and carbonatable element plant nutrients such as K, P, S, B, Co, Cu, Fe, Mo, Zn and Ni are used by the crop plants as nutrients. Carbonatable elements such as Ca, Mg, K, Na and Fe react with $CO_2$ from the hyaloclastite, in the ground and the air to create simple or complex carbonated mineral, thereby mineralizing $CO_2$.

Example 12

Hyaloclastite is processed in the same manner as described in Example 1 above. The hyaloclastite is blended with a carbonation aid and the combination is exposed to carbon dioxide gas in the screw conveyor 20. The carbon dioxide gas comes from the flue gas from a cement kiln. The combined hyaloclastite and carbonation aid from the storage silo 26 is then blended with an alkaline or basic soil. The soil is tilled and a crop is planted. Water from rain or irrigation is provided to the soil and the hyaloclastite reacts with the soil solution releasing nutrients and carbonatable minerals. The plant nutrients are absorbed by the crop and the carbonatable minerals released from the hyaloclastite react with $CO_2$ absorbed/adsorbed on the hyaloclastite, in the ground, air and from the carbonation aid. Elements weathered into the separate plant nutrients and carbonatable elements. Plant nutrients such as K, P, S, B, Co, Cu, Fe, Mo, Zn and Ni are used by the crop plants as nutrients. Carbonatable elements such as Ca, Mg, K, Na and Fe react with $CO_2$ in the ground and the air to create simple or complex carbonated minerals, thereby mineralizing $CO_2$. The $CO_2$ adsorbed on the hyaloclastite and carbonation aid react with the carbonatable elements as the plant nutrient is weathered and elements are dissolved in soil are mineralized within the soil by carbonating the carbonatable elements.

It should be understood, of course, that the foregoing relates only to certain disclosed embodiments of the present invention and that numerous modifications or alterations may be made therein without departing from the spirit and scope of the invention.

What is claimed is:
1. A method comprising:
   screening or reducing in size basaltic hyaloclastite or intermediate basaltic hyaloclastite to a volume-based mean particle size of less than or equal to approximately 100 μm, wherein the basaltic hyaloclastite or intermediate hyaloclastite has an amorphous content of approximately 10% to 100% by weight; and, combining the screened or size reduced basaltic hyaloclastite or intermediate hyaloclastite with soil.

2. The method of claim 1, wherein the basaltic hyaloclastite or intermediate basaltic hyaloclastite has a volume-based mean particle size of less than or equal to approximately 60 µm.

3. The method of claim 1, wherein the basaltic hyaloclastite or intermediate basaltic hyaloclastite has a volume-based mean particle size of less than or equal to approximately 45 µm.

4. The method of of claim 1, wherein the basaltic hyaloclastite or intermediate basaltic hyaloclastite has a volume-based mean particle size of less than or equal to approximately 15 µm.

5. The method of claim 1, wherein the basaltic hyaloclastite or intermediate hyaloclastite has an amorphous content of approximately 20% to 100% by weight.

6. The method of claim 5, wherein the basaltic hyaloclastite or intermediate basaltic hyaloclastite has a volume-based mean particle size of less than or equal to approximately 60 µm.

7. The method of claim 5, wherein the basaltic hyaloclastite or intermediate basaltic hyaloclastite has a volume-based mean particle size of less than or equal to approximately 45 µm.

8. The method of claim 5, wherein the basaltic hyaloclastite or intermediate basaltic hyaloclastite has a volume-based mean particle size of less than or equal to approximately 15 µm.

9. The method of claim 1, wherein the basaltic hyaloclastite or intermediate hyaloclastite has an amorphous content of approximately 30% to 100% by weight.

10. The method of claim 9, wherein the basaltic hyaloclastite or intermediate basaltic hyaloclastite has a volume-based mean particle size of less than or equal to approximately 60 µm.

11. The method of claim 9, wherein the basaltic hyaloclastite or intermediate basaltic hyaloclastite has a volume-based mean particle size of less than or equal to approximately 45 µm.

12. The method of claim 1, wherein the basaltic hyaloclastite or intermediate hyaloclastite has an amorphous content of approximately 40% to 100% by weight.

13. The method of claim 12, wherein the basaltic hyaloclastite or intermediate basaltic hyaloclastite has a volume-based mean particle size of less than or equal to approximately 60 µm.

14. The method of claim 12, wherein the basaltic hyaloclastite or intermediate basaltic hyaloclastite has a volume-based mean particle size of less than or equal to approximately 45 µm.

15. The method of claim 1, wherein the basaltic hyaloclastite or intermediate hyaloclastite has an amorphous content of approximately 50% to 100% by weight.

16. The method of claim 15, wherein the basaltic hyaloclastite or intermediate basaltic hyaloclastite has a volume-based mean particle size of less than or equal to approximately 60 µm.

17. The method of claim 15, wherein the basaltic hyaloclastite or intermediate basaltic hyaloclastite has a volume-based mean particle size of less than or equal to approximately 45 µm.

18. The method of claim 1, wherein the basaltic hyaloclastite or intermediate hyaloclastite has an amorphous content of approximately 60% to 100% by weight.

19. The method of claim 18, wherein the basaltic hyaloclastite or intermediate basaltic hyaloclastite has a volume-based mean particle size of less than or equal to approximately 60 µm.

20. The method of claim 18, wherein the basaltic hyaloclastite or intermediate basaltic hyaloclastite has a volume-based mean particle size of less than or equal to approximately 45 µm.

* * * * *